(12) United States Patent
Berkes et al.

(10) Patent No.: US 10,004,772 B2
(45) Date of Patent: *Jun. 26, 2018

(54) MATERIALS AND METHODS FOR IMPROVING IMMUNE RESPONSES AND SKIN AND/OR MUCOSAL BARRIER FUNCTIONS

(71) Applicant: Quorum Innovations, LLC, Sarasota, FL (US)

(72) Inventors: Eva A. Berkes, Sarasota, FL (US); Nicholas T. Monsul, Sarasota, FL (US); Frederick T. Boehm, Sarasota, FL (US)

(73) Assignee: QUORUM INNOVATIONS, LLC, Sarasota, FL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/496,686

(22) Filed: Apr. 25, 2017

(65) Prior Publication Data
US 2017/0224748 A1 Aug. 10, 2017

Related U.S. Application Data

(63) Continuation of application No. 15/226,226, filed on Aug. 2, 2016, now Pat. No. 9,706,778, which is a continuation of application No. PCT/US2016/042939, filed on Jul. 19, 2016.

(60) Provisional application No. 62/194,630, filed on Jul. 20, 2015.

(51) Int. Cl.
| | |
|---|---|
| *A61K 35/66* | (2015.01) |
| *A61K 35/747* | (2015.01) |
| *A01N 63/00* | (2006.01) |
| *A01N 63/02* | (2006.01) |
| *C12R 1/225* | (2006.01) |
| *A23L 33/135* | (2016.01) |

(52) U.S. Cl.
CPC ............ *A61K 35/747* (2013.01); *A01N 63/00* (2013.01); *A01N 63/02* (2013.01); *A23L 33/135* (2016.08); *C12R 1/225* (2013.01); *A23V 2002/00* (2013.01); *A23Y 2220/35* (2013.01)

(58) Field of Classification Search
None
See application file for complete search history.

(56) References Cited

U.S. PATENT DOCUMENTS

| | | | |
|---|---|---|---|
| 9,706,778 B2 * | 7/2017 | Berkes | A01N 63/00 |
| 2010/0086520 A1 * | 4/2010 | Reindl | A01N 63/00 |
| | | | 424/93.3 |

FOREIGN PATENT DOCUMENTS

| | | |
|---|---|---|
| CN | 102226157 A | 10/2011 |
| WO | WO 2009/071086 A2 | 6/2009 |

OTHER PUBLICATIONS

Aoudia, N. et al., "Biofilms of Lactobacillus plantarum and Lactobacillus fermentum: Effect on stress responses, antagonistic effects on pathogen growth and immunomodulatory properties." *Food Microbiology*, Feb. 2015, 53(Pt. A): Abstract.
Devine, D. A. et al., "Prospects for the development of probiotics and prebiotics for oral applications." *Journal of Oral Microbiology*, Feb. 2009, 1: 1-11.
Donlan, R. M., Costerton, J.W., "Biofilms: Survival Mechanisms of Clinically Relevant Microorganisms." *Clinical Microbiology Reviews*, Apr. 2002, 15(2): 167-193, DOI: 10.1128/CMR.15.2.167-193.2002.
Kim, Y. et al., "Released exopolysaccharide (r-EPS) produced from probiotic bacteria reduce biofilm formation of enterohemorrhagic *Escherichia coli* O157:H7." *Biochemical and Biophysical Research Communications*, 2009, 379: 324-329, doi:10.1016/j.bbrc.2008.12.053.
Subhadra, B. et al., "Draft whole-genome sequence of Lactobacillus fermentum LfQi6, derived from the human microbiome." *Genome Announcements*, May/Jun. 2015, 3(3): 1-2.

* cited by examiner

*Primary Examiner* — Chris R Tate
*Assistant Examiner* — Randall Winston
(74) *Attorney, Agent, or Firm* — Saliwanchik, Lloyd & Eisenschenk

(57) ABSTRACT

The subject invention provides compositions and methods for treating human dermatological conditions by employing a microbiome-centered treatment approach. Preferred embodiments of the invention provide pharmaceutical and cosmetic compositions, and the methods of using the same, comprising a strain of *Lactobacillus fermentum* bacterium, or bioactive extracts thereof, derived from human microbiota and capable of growing in biofilm phenotype.

10 Claims, 16 Drawing Sheets

Step-1
Biofilm phenotype LfQi6
in frozen stock is cultured in
10 ml fresh MRS media for 24h
at 37C

Step-2
Inoculate 10 ml culture into 25 L
MRS media with 500 g sterile glass
wool

Step-3
Culture it for 72 g in
static conditions at 37C
Mix the culture every 24h
with a gentle shaking

Step-4
Harvest the media and glass
Wool. Sonicate the glass wool
to detach biofilm cells.

Step-5
Centrifuge the cells to concentrate
the biofilm LfQi6. Suspend in sterile
Water
Yied: 50g/25 Liter culture

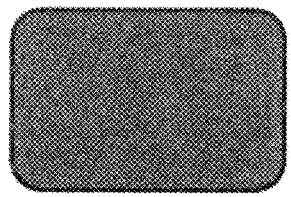

FIG. 2

Step-1
50g Biofilm phenotype LfQi6
is suspended in 1 liter sterile
Water. Gentle mixed for 24 hr
at room temperature to

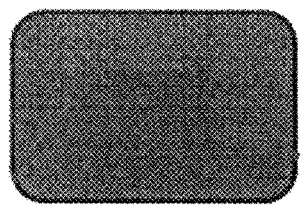

Step-2
Gentle mixed for 24 hr
at room temperature for
passive release of multiple
bioactives

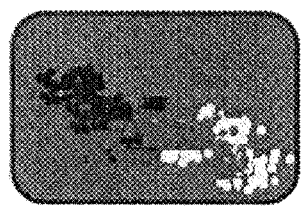

Step-3
The mixture is then sonicated
for 30 min (50 KHz, 200 watt) using
OmniSonic Ruptor 400 in into niform
lysate

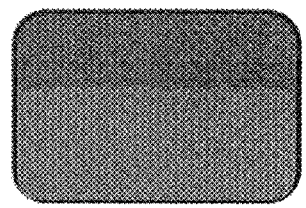

Step-4
The sonicated lysate is frozen

Step-5
The frozen lysate
is lyophilized into a fine
powder

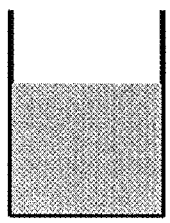

FIG. 3

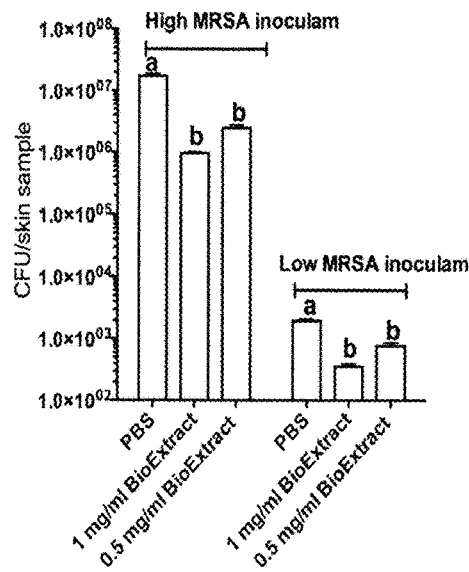
FIG. 13
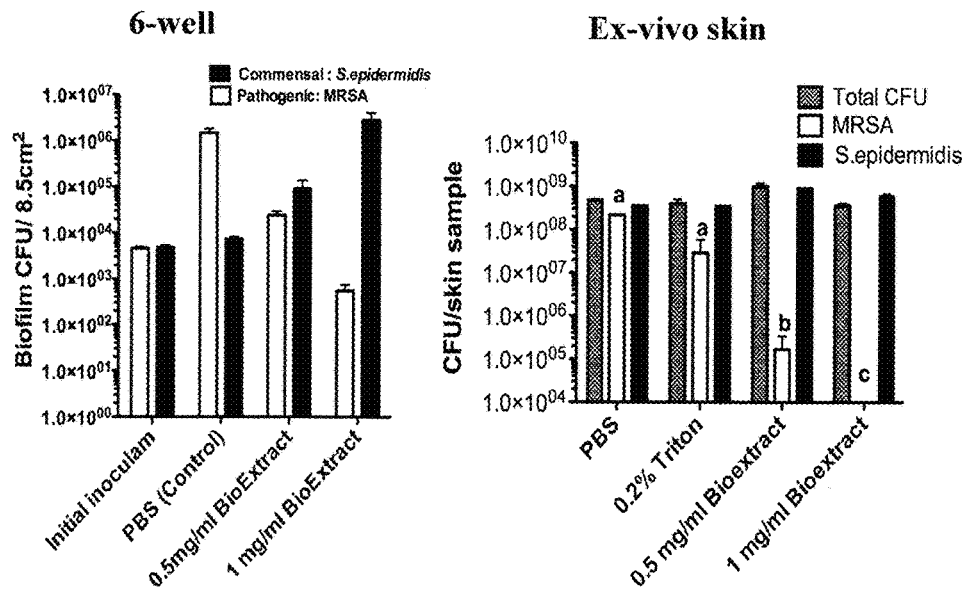
FIG. 14A                    FIG. 14B

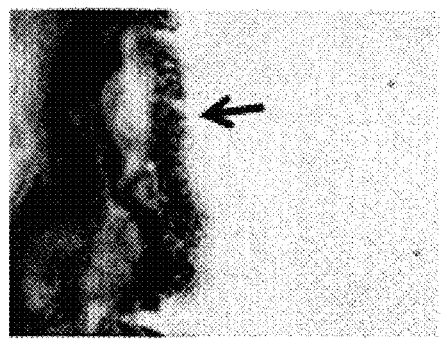
FIG. 18E
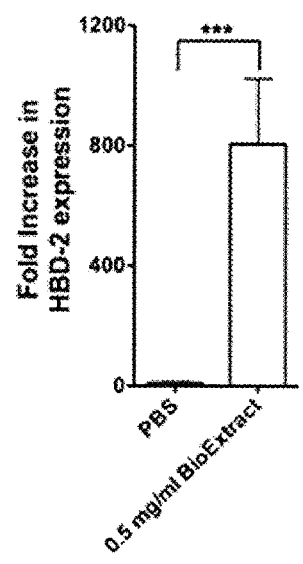 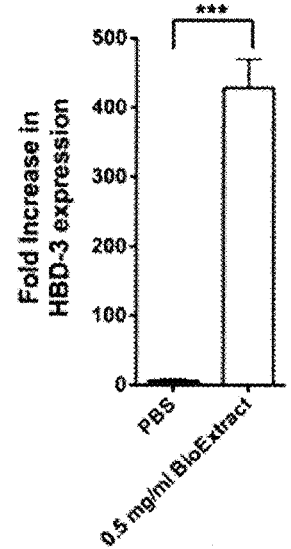
FIG. 19A  FIG. 19B

MATERIALS AND METHODS FOR IMPROVING IMMUNE RESPONSES AND SKIN AND/OR MUCOSAL BARRIER FUNCTIONS

CROSS-REFERENCE TO A RELATED APPLICATION

This application is a continuation application of co-pending U.S. application Ser. No. 15/226,226, filed Aug. 2, 2016; which is a continuation of International Application No. PCT/US2016/042939, filed Jul. 19, 2016; which claims the benefit of U.S. Provisional Application Ser. No. 62/194,630, filed Jul. 20, 2015, all of which are incorporated herein by reference in their entirety.

BACKGROUND OF THE INVENTION

With its diverse resident commensal microbiota, the human microbiome has received substantial attention for the critical roles it plays in health and disease.

An initial line of defense against foreign invaders, the skin is home to a diverse population of microbes. These microbes include resident commensals, transients and pathogens. In order to survive in the challenging environment of the skin, microbes often exhibit a biofilm phenotype, which gives competitive advantages for survival and growth. Many skin pathogens can be found living on the skin as commensals; microbial dysbiosis, host genetic variation, and immune status may drive the transition from commensal to pathogen.

Atopic dermatitis (AD) is a multifactorial chronic inflammatory skin disease involving genetic factors, such as filaggrin deficiency (1), and environmental triggers, including *Staphylococcus aureus*, and is often the initial presentation of the "allergic march." Worldwide, AD affects approximately 20% of children and 5% of adults, typically presenting clinically as chronically dry, pruritic eczematous dermatitis with episodic acute flares. AD is frequently associated with asthma and allergic rhinitis. Quality of life for individuals affected by AD is significantly disrupted, and there is a heavy economic burden associated with the disease, with estimates of annual national direct costs ranging from 364M USD to 3.8B USD (4,5). AD represents a large, unmet need for more effective therapeutics.

Commensal bacteria like *S. epidermidis* have several antibacterial mechanisms to ward-off pathogenic bacteria. Several studies have shown serine proteins from commensal *S. epidermidis* prevent the growth of pathogenic strains of *S. aureus* (40,41). A novel lipopeptide from commensal *Staphylococcus epidermidis* increases HβD2 and HβD3 via TLR2/CD36-MAPK, thus enhancing antimicrobial defense against pathogenic infections (42,43). Other studies have shown that *S. epidermidis* in the human skin microbiome produces secondary fermentation metabolites to inhibit the growth of additional pathogenic bacterial strains (44). Further, enhancing commensals such as *S. epidermidis* might have other beneficial roles, too. For example, skin *S. epidermidis* have an autonomous role in controlling the local inflammatory milieu and tuning resident T lymphocyte function, thereby rendering protective immunity to a cutaneous pathogen (45).

Skin dysbiosis has been linked with common skin conditions, including AD, acne and rosacea (21). Skin microbiome sequencing during acute AD flares has correlated increased levels of the pathogen *S. aureus* and the commensal *S. epidermidis* during flares, with subsequent decrease during application of standard medical treatments such as topical steroids and antibiotics (22).

Skin dysbiosis can initiate key biochemical and immune triggers, and studies have found an association between high amounts of staphylococcal bacteria and clinical worsening of AD lesions; for instance, patients harboring MRSA had greater total body clinical dermatitis scores (15,29-31).

Lipoteichoic acid exerts immunological effects mainly through TLR 2 (32-34) that could implicate it in the worsening of atopic dermatitis (31,35). Studies showed that in a pediatric population of AD patients, temporal shifts in the skin microbiota occur over three disease stages: baseline, flare, and post flare as compared to healthy controls. In particular, lesional skin bacterial diversity decreased during the flare stage, parallel with increased relative abundance of *S. aureus*, but increased during the post flare status, indicative of a link between disease severity and microbial diversity (21,22).

Filaggrin deficiency, *Staphylococcus aureus* colonization, defective innate immunity and skin microbial dysbiosis are the major underlying factors in the progression of the disease. Up to 90% of individuals with AD are colonized with *S. aureus*; prevalence of MRSA in AD ranges from 10-30.8% (15).

The role of the skin barrier in the pathogenesis of AD is now clear (18-20). In this context, the strongest genetic association with AD so far has been demonstrated for loss-of-function mutations in the filaggrin (FLG) gene, which encodes the important barrier protein (pro-filaggrin) (8,9). Filaggrin plays several roles in the pathophysiology of AD which explains why lower expression of a single component of the epidermal differentiation complex might have such a great influence on the whole function of the skin barrier. Skin barrier function is a major determinant of the equilibrium of skin commensal flora. The skin barrier protein FLG ensures that pathogenic strains of bacteria are not penetrating into deeper layers. In a recent study filaggrin knockout resulted in significantly increased epidermal *S. aureus* colonization, as well as in an up-regulation of *S. aureus*-induced IL-8 expression (16).

However, the FLG mutation is absent in most AD individuals; secondary filaggrin deficiency is common in AD (6). This has been postulated to be due to various environmental factors, such as the Th2/Th22 cytokine milieu common in AD inflammation, bacterial exotoxins, AD skin dysbiosis associated with cutaneous *S. aureus* and methicillin-resistant *S. aureus* (MRSA), mechanical damage associated with scratching, skin dehydration and topical irritants (9-14).

Lower filaggrin levels in AD predispose to *S. aureus* colonization (11,12) and lower levels of antimicrobial peptides are associated with defective innate immunity and increased extracellular adhesins for *S. aureus* (16,17).

Controlling pathogenic biofilm and its metabolic products on skin is a major component in restoring the symbiosis of commensal skin flora and skin health. Current therapeutics, however, focus mainly on symptom-control rather than modulating the overall microbiome to inhibit the growth and reduce the adhesion and attachment of pathogenic biofilm activities, while promoting the growth of commensal biofilm on human skin.

SUMMARY OF THE INVENTION

The subject invention provides compositions and methods for treating human dermatological (and other) conditions by employing a microbiome-centered treatment approach. Preferred embodiments of the invention provide pharmaceutical and cosmetic compositions, and methods of using the same.

In preferred embodiments, the compositions comprise a strain of *Lactobacillus fermentum* bacterium, or a bioactive extract thereof. In preferred embodiments, extracts of the bacteria are obtained when the bacteria are grown as biofilm. The subject invention also provides compositions comprising *L. fermentum* bacterium, or bioactive extracts thereof, in a lyophilized, freeze dried, and/or lysate form.

In some embodiments of the subject invention the enhancement of skin barrier functions is achieved by upregulating the expression of skin barrier proteins utilizing the bacterial compositions of the subject invention. In other embodiments, the enhancement of skin innate immune functions is provided by modulating the expression of skin innate immune peptides and/or inflammatory cytokines utilizing the bacteria and compositions of the subject invention.

In another aspect, the subject invention provides a method of treating human dermatological disorders, comprising administering to a subject a therapeutically effective amount of the composition, wherein the composition preferably comprises one or more bioactive extracts of the Lf Qi6 biofilm.

Advantageously, preferred compositions and treatment methods provided herein are effective in treating human skin barrier dysfunctions, dysbiosis, skin innate immune dysfunctions, and/or inflammatory skin diseases, as well as improving the appearance and/or the texture of the skin. Subjects treated according to the subject invention can experience relieved symptom severity, reduced incidence of acute flares, and improved quality of life.

In one aspect, the subject invention provides a therapeutic composition for treating human dermatological disorders, comprising a bacterial strain, or a bioactive extract therefrom, and a pharmaceutically acceptable excipient. The composition preferably has one or more biological activities selected from inhibiting anti-microbial activity, pathogenic biofilm growth, inhibiting pathogenic biofilm adhesion, promoting pathogenic biofilm detachment, promoting commensal biofilm growth, enhancing skin barrier functions, and enhancing skin innate immune functions.

In exemplary embodiments, the pathogenic bacterium is methicillin-resistant *Staphylococcus aureus* (MRSA) and the commensal bacterium is *Staphylococcus epidermidis* (*S. epidermidis*).

In some embodiments, the bacterial strain is *Lactobacillus fermentum* Qi6, also referred to herein as Lf Qi6. In one embodiment, the subject invention provides an isolated or a biologically pure culture of Lf Qi6. In another embodiment, the subject invention provides a biologically pure culture of Lf Qi6, grown as a biofilm. Specifically taught herein are methods for inducing and identifying the biofilm phenotype. Further provided herein are methods of utilizing the biofilm phenotype, as well as extracts of the biofilm phenotype, and lysates thereof. In preferred embodiments, the pharmaceutical compositions comprise bioactive extracts of Lf Qi6 biofilm.

In a further aspect, the subject invention provides a cosmetic composition for improving human skin conditions, comprising Lf Qi6, and/or a bioactive extract thereof, and together with one or more cosmetically acceptable excipients. In preferred embodiments, the cosmetic composition comprises bioactive extracts of Lf Qi6 biofilm.

In some embodiments, the cosmetically acceptable excipients comprise substances used for formulations selected from lotion, cream, emulsion, ointment, oil, gel, serum, and combinations thereof.

In yet another aspect, the subject invention provides a method of improving human skin conditions, comprising administering to a subject an effective amount of a composition comprising a bacterial strain, and/or a bioactive extract thereof, and one or more cosmetically acceptable excipients. As with the therapeutic composition, the cosmetic composition preferably has one or more biological activities selected from inhibiting pathogenic biofilm growth, inhibiting pathogenic biofilm adhesion, promoting pathogenic biofilm detachment, promoting commensal biofilm growth, enhancing skin barrier functions, enhancing skin innate immune functions, and combinations thereof. In preferred embodiments, the bacterial strain is Lf Qi6.

BRIEF DESCRIPTION OF THE FIGURES

FIG. 2 illustrates a Lf Qi6 Scale-up Culture Procedure. Step 1: Biofilm phenotype Lf Qi6 is cultured in 10 ml fresh MRS medium for 24 hour at 37°; Step 2: Inoculate 10 ml culture into 25 L MRS medium with 500 g sterile glass wool; Step 3: Culture it for 72 hours in static conditions at 37° C. Mix the culture every 24 hours with a gentle shaking; Step 4: Harvest the medium and glass wool. Sonicate the glass wool to detach biofilm cells; Step 5: Centrifuge the cells to concentrate the biofilm Lf Qi6. Suspend in sterile water.

FIG. 3 illustrates an example of Lf Qi6 downstream processing. Step 1: 50 g biofilm phenotype Lf Qi6 is suspended in 1 L of sterile water; Step 2: The suspension is gently mixed for 24 hours at room temperature for passive release of bioactive substances; Step 3: the mixture is then sonicated for 30 minutes (50 KHz, 200 watt) into a uniform lysate using an OmniSonic Ruptor 400; Step 4: the sonicated lysate is frozen; Step 5: the frozen lysate is lyophilized into a fine powder.

FIG. 13 illustrates that LfQi507 rapidly detaches MRSA biofilm in an ex vivo human skin organotypic culture system.

FIG. 14A illustrates the modulation of pathogenic MRSA vs. commensal S. epidermidis by Lf Qi601 biofilm in a co-culture model in a 6-well plate in vitro. FIG. 14B illustrates the modulation of pathogenic MRSA vs. commensal S. epidermidis by Lf Qi601 biofilm in a co-culture model in ex-vivo skin explant. Data is represented as the mean±SEM (standard error of means) and one-way ANOVA was used to determine differences among treatment means ($P < 0.05$). Means with the same letter are not significantly different from each other ($P<0.05$, Newman-Keuls multiple comparison test).

FIG. 15A shows the isotype control without treatment of the Lf Qi6 bioextract. FIG. 15B shows the PBS-base line. FIG. 15C is an ex-vivo skin explant treated with 0.5 mg/mL of Lf Qi6 bioextract. FIG. 15D is an ex-vivo skin explant treated with 1 mg/mL of Lf Qi6 bioextract. FIG. 15E shows the quantitative immunoratio of skin explants treatment with PBS, 0.5 mg/mL of Lf Qi6 bioextract, or 1 mg/mL Lf Qi6 bioextract. FIG. 15F shows the quantitative FLG ELISA of skin explants treatment with PBS, 0.5 mg/mL of Lf Qi6 bioextract, or 1 mg/mL Lf Qi6 bioextract. Data is represented as the mean±SEM (standard error of means) and one-way ANOVA was used to determine differences among treatment means ($P<0.05$).  denotes $P<0.01$ and * denotes $P<0.001$.

FIG. 18E shows the MRSA biofilm formed on ex-vivo skin stained with hematoxylin-eosin, the arrow indicating robust biofilm formation. Data is represented as the mean SEM (standard error of means) and one-way ANOVA was used to determine differences among treatment means ($P<0.05$). When significant differences were found, means were compared using Newman-Keuls multiple comparison test. Means with the same letter are not significantly different from each other.

FIG. 19A represents the upregulation of human beta-defension 2 by the Lf Qi6 bioextracts.

FIG. 19B shows the upregulation of human beta-defension 3 in ex-vivo skin model treated with LfQi6 bioextracts.

DETAILED DESCRIPTION OF THE INVENTION

Figure 1:
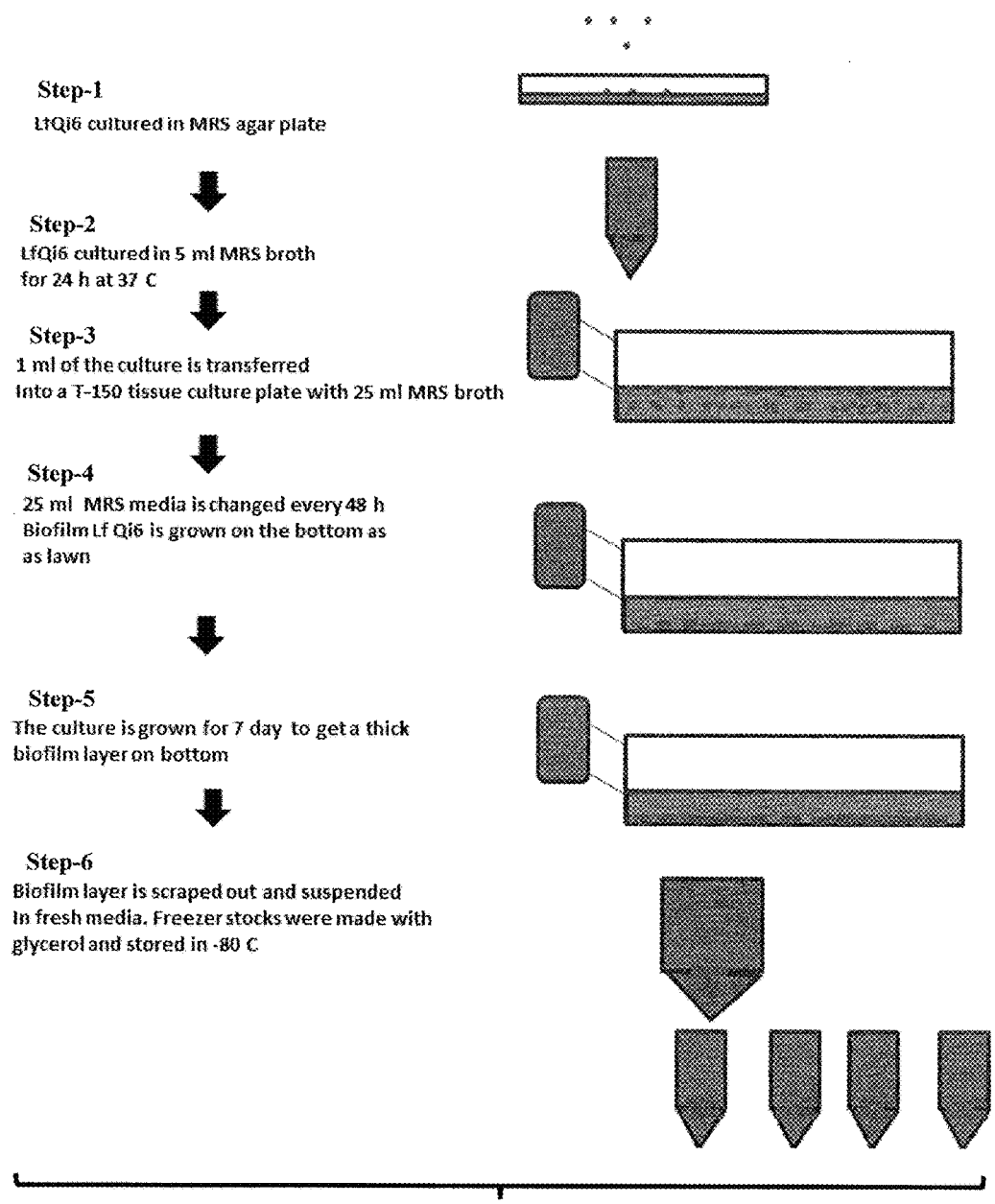
FIG. 1 shows a Lf Qi6 Culture procedure. Step 1: Lf Qi6 cultured in MRS agar plate; Step 2: Lf Qi6 cultured in 5 ml MRS broth for 24 hour at 37° C.; Step 3: 0.1 ml of the culture is transferred into a T-150 tissue culture plate with 25 ml MRS broth; Step 4: 25 ml MRS media is changed every 48 hours, biofilm Lf Qi6 is grown on the bottom as lawn; Step 5: the culture is grown for 7 days to get a thick biofilm layer on bottom; Step 6: Biofilm layer is scraped out and suspended in fresh medium. Freezer stocks can be made with glycerol and stored in −80°.

The subject invention provides compositions and methods for treating human dermatological conditions. Preferred embodiments of the invention provide pharmaceutical and cosmetic compositions, and methods of using the same, comprising a strain of *Lactobacillus fermentum* bacterium, and/or one or more bioactive extracts thereof, derived from human microbiota and capable of growing in biofilm phenotype. The subject invention also provides compositions comprising *L. fermentum* bacterium, and/or bioactive extracts thereof, in a lyophilized, freeze dried, and/or lysate form.

Advantageously, preferred compositions and treatment methods provided herein are effective in treating human skin barrier dysfunctions, dysbiosis, skin innate immune dysfunctions, inflammatory skin diseases, as well as improving the appearance and/or texture of the skin. Subjects thus treated with this microbiome-centered approach can experience relieved symptom severity, reduced incidence of acute flares, and improved quality of life.

In some embodiments, the bacterial strain is *Lactobacillus fermentum* Qi6, also referred to herein as Lf Qi6. In one embodiment, the subject invention provides an isolated or a biologically pure culture of Lf Qi6. In another embodiment, the subject invention provides a biologically pure culture of Lf Qi6, grown as a biofilm. Specifically taught herein are methods for inducing and identifying the biofilm phenotype. Further provided herein are methods of utilizing the biofilm phenotype, as well as extracts of the biofilm phenotype, including lysates thereof. In preferred embodiments, the pharmaceutical compositions comprise bioactive extracts of Lf Qi6 biofilm.

A culture of the *L. fermentum* microbe has been deposited with the American Type Culture Collection (ATCC), 10801 University Blvd., Manassas, Va. 20110-2209 USA. The deposit has been assigned accession number ATCC No. PTA-122195 by the repository and was deposited on Jun. 10, 2015.

The subject culture has been deposited under conditions that assure that access to the culture will be available during the pendency of this patent application to one determined by the Commissioner of Patents and Trademarks to be entitled thereto under 37 CFR 1.14 and 35 U.S.C 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

As used herein, reference to an "isolated" microbe refers to one that has been removed from materials with which it exists in nature. The microbe may be isolated from, for example, soil, blood, mucous, or milk such that it is removed from, and is no longer mixed or otherwise associated with, those materials to the extent that it is in nature. Such isolation can be used to impart upon the microbe markedly different characteristics, such as the production of different, or different amounts of, compounds, compared to what the microbe exhibits in its natural state.

In one aspect, the subject invention provides a pharmaceutical composition for treating human dermatological disorders, comprising a biologically pure bacterial strain, and/or a bioactive extract thereof, and one or more pharmaceutically acceptable excipients, the bacterial strain and its extract being capable of growing in both planktonic and biofilm phenotypes, the composition having one or more biological activities selected from, general antimicrobial activity, inhibiting pathogenic biofilm growth, inhibiting pathogenic biofilm adhesion, promoting pathogenic biofilm detachment, promoting commensal biofilm growth, enhancing skin barrier functions, and enhancing skin innate immune functions.

As used herein the term "extract" refers to a composition obtained by processing a biofilm culture. The processing may involve, for example, physical and/or chemical treatment. The physical and/or chemical treatment may comprise, for example, filtering, centrifugation, sonication, pressure treatment, radiation treatment, lysing, treatment with solvents or other chemicals, and combinations of these treatments. The extract can be in the form of, for example, a supernatant such as that produced via centrifugation. The extract can also include cell mass obtained through centrifugation. The cells may be intact or not intact, viable or not viable. The extract may comprise cell membrane components and/or intracellular components. In certain embodiments, the extract is at least 80, 85, 90, or 95%, by weight, cell mass. In certain embodiments, at least 95% of the intact cells are non-viable. In certain embodiments, less than 10% of the cell mass in the extract is intact cells.

Human skin comprises two compartments, the deep compartment (the dermis) and the surface compartment (the epidermis). The skin constitutes a barrier against external attacks, particularly chemical, mechanical, or infectious attacks, as well as a number of defensive reactions against environmental factors such as, for example, climate, ultraviolet rays, and tobacco, and/or xenobiotic factors, such as, for example, microorganisms. This property is referred to as the skin barrier function and is mainly provided by the most superficial layer of the epidermis, namely the horny layer, referred to as the stratum corneum. Detrimental changes in the barrier can be reflected by, for example, cutaneous discomfort, sensory phenomena and/or cutaneous dryness.

Compositions according to some embodiments of the invention are useful for preventing a reduction in the barrier function and/or to repair or regenerate barrier function. Disorders associated with disruption of the skin and/or mucosal barrier include, but are not limited to, psoriasis, icthyosis, sarcoidosis, atherosclerosis, inflammatory bowel disease, acne (including hiradenitis suppurativa), burns, diaper rash, Netherton's syndrome, actinic keratosis, dermatomycoses, dermatosis or ectodermal dysplasia, atopic dermatitis, contact dermatitis, seborrehic dermatitis, vulgaris, eosinophilic esophagitis, filaggrin deficiency, and other disorders associated with damage or breakdown of the skin and/or mucosal barrier.

In some embodiments, repair or regeneration of the barrier includes repair or regeneration of a mucous membrane. Mucous membranes include mucosa of the mouth (including mucosa of the cheek, the soft palate, the tongue, including the under surface of the tongue and the floor of the mouth), the nose, the throat (including mucosa of the pharynx, the larynx, the trachea and the esophagus), the bronchi, the lungs, the eye, the ear, the gastrointestinal tract, the vagina, the penis, the urethra, the bladder, and the anus. In certain embodiments, the compositions of the subject invention can also be used in the treatment of acute and chronic viral infections. In particular, the treatment of chronic Epstein-Barr virus, cytomegalovirus and other herpes-type virus infection, which are ubiquitous in the population and are associated with a decrease on the immune survillance.

The pharmaceutical compositions provided herein may also include other pharmaceutically-acceptable ingredients known to those skilled in the art, including, but not limited to, pharmaceutically-acceptable carriers, adjuvants, excipients, diluents, fillers, buffers, preservatives, anti-oxidants, lubricants, stabilisers, solubilisers, surfactants (e.g., wetting agents), masking agents, and colouring agents. The formulations may further comprise other active agents including, for example, other therapeutic or prophylactic agents.

As provided herein, "pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable excipient, carrier or adjuvant" refers to an excipient, carrier or adjuvant that can be administered to a subject, together with an active ingredient, and which does not destroy the pharmacological activity thereof and is nontoxic when administered in doses sufficient to deliver a therapeutic amount of the compositions provided herein.

In some embodiments, the biologically pure strain is *Lactobacillus ferment* Qi6, hereafter also referred to as Lf Qi6. In preferred embodiments, the pharmaceutical compositions provided herein comprise one or more bioactive extracts of Lf Qi6 obtained after it has been grown in the biofilm phenotype.

"Planktonic" refers to a phenotype typical to microorganisms (bacteria, fungi, and/or protozoa, with associated bacteriophages and other viruses) that float freely in a liquid medium. A "biofilm," on the other hand, is an accumulation of microorganisms embedded in an extracellular polymeric matrix (EPS) and adherent to solid biological or non-biotic surfaces. It has been observed and reported in the examples provided herein that Lf Qi6 can form biofilm in addition to possessing the typical planktonic phenotype.

Methods for growing biofilm are known in the art and are described in, for example, WO 2012/118535, which is incorporated herein, in its entirety, by reference, including the publications cited in that reference, such as those cited at pages 26-31.

Whereas biofilms of pathogenic bacteria such as *Staphylococcus aureus* (*S. aureus*) can cause highly resistant bacterial infections, biofilms of Lf Qi6 and extracts thereof have been found to have anti-dysbiotic and anti-biofilm (e.g., of pathogenic bacteria) properties, skin barrier enhancement, and immunomodulatory effects on human keratinocytes and ex-vivo human skin cultures.

Furthermore, co-culture studies have shown that 0.5-1.0 mg/ml of Lf Qi6 biofiom extracts reduce the burden of pathogenic biofilm on the skin while promoting commensal bacteria growth. Enhancing the relative proportion of resident commensal bacteria can decrease the load of pathogenic biofilm on surfaces.

In exemplary embodiments, the pathogenic bacterium is methicillin-resistant *Staphylococcus aureus* (MRSA) and the commensal bacterium is *Staphylococcus epidermidis* (*S. epidermidis*).

Infections occur where disease causing microorganisms invade the tissues of the body. Those microorganisms and the toxins that they produce react with the tissues of the body, often causing immune reactions by the infected host. Infections may be caused by bacteria, viruses, viroids, fungi and other parasites. Infections may occur via any of the tissues of the body, such as the skin, gut or membranes. In specific embodiments, the subject invention provides compositions for the treatment and/or prevention of infection of the external surface of the body, and particularly of the skin. The infection may be caused by a bacterium, such as pathogenic *Staphylococcus* bacteria. The pharmaceutical compositions provided herein may be applied separately, sequentially or simultaneously with exposure to the infective agent, such as MRSA. In other embodiments, the subject invention provides materials and methods for treating intestinal and other internal disorders.

*S. aureus* is a transient colonizer of skin predominantly in the moist, warm regions of the body such as the groin, axilla and the anterior nares. Up to 60% of the population are intermittent carriers while another 20% may be stably colonized. While normal carriage is asymptomatic, *S. aureus* may invade tissues (e.g., through broken skin) where it causes diseases ranging from the relatively minor impetigo and scalded skin syndrome, to life threatening conditions such as septicaemia. Furthermore, *S. aureus* infection is often a secondary phenomenon in skin with underlying conditions such as atopic dermatitis (AD).

Exemplary compositions provided by the subject invention are useful for the treatment of infections by a number of pathogenic bacteria including, but not limited to, *Staphylococcus* spp., *Pseudomonas* spp., *Staphyloccus saprophyticus, Staphyloccocus xylosus, Staphyloccocus lugdunensis, Staphyloccocus schleiferi, Stapylococcus caprae, Staphylococcus saprophyticus, Staphylococcus hominis, Staphylococcus aureus, Enterococcus faecalis,* vancomycin-resistant *Enterococcus* (VRE), *Bacillus cereus, Bacillus subtilis, Listeria monocytogenes, Streptococcus pyrogenes, Streptococcus salivariu, Streptococcus mutans,* and *Streptococcus pneumonia*. Other pathogenic bacteria will be readily recognized by a person skilled in the art.

Certain compositions provided herein exhibit anti-*S. aureus*, preferably MRSA, activity, and are thus useful for the treatment or prevention of *S. aureus* infection, including the inhibition of bacterial growth, inhibition of bacterial adhesion, and promotion of bacterial detachment.

In accordance with the subject invention, Lf Qi6 has been found to have anti-adhesive, inhibition and detachment activities against MRSA biofilm, both in vitro and in a living ex-vivo human skin explant model. There are several potential mechanisms for Lf Qi6 MRSA anti-biofilm activity. For instance, Lf Qi6, or its extracts, may contain anti-biofilm peptides or heat shock proteins, and/or (p)ppGpp-blockers. Proteomic analysis from a whole genome sequencing of Lf Qi6 suggests several unique heat shock proteins and other related stress proteins.

Some embodiments of the subject invention provide that the enhancement of skin barrier function is achieved by upregulating the expression of skin barrier proteins. In other embodiments, the enhancement of skin innate immune functions is provided by modulating the expression of skin innate immune peptides and/or inflammatory cytokines.

In some embodiments, bioactives extracted from Lf Qi6 biofilm have agonistic activities towards peroxisome proliferator-activated receptors (PPARs), namely, PPAR-alpha, PPAR-beta/delta, and/or PPAR-gamma. PPARs are a group of nuclear receptor proteins and serve as transcription factors to regulate gene expression in response to various physiological stimuli. Their structure is highly conserved, composed of an amino-terminal activation domain (AF1), a zinc-finger DNA binding domain, a ligand-binding carboxy-terminal domain and a second activation domain at the c-terminus (AF2).

PPAR-alpha is expressed in metabolically active tissues such as brown fat, liver, heart, muscle, kidney, immune cells. Its ligands include docosahexanoic acid (DHA), WY 14643, clofibrate, oxidized phospholipids, phthalate esters, and various herbicides. The first three ligands are known to increase filaggrin and heat shock protein 27 (HSP27). PPAR-alpha is a major regulator of hepatic lipid metabolism, activated under conditions of energy deprivation to initiate ketogenesis, an adaptation to prolonged fasting. PPAR-alpha synthetic ligands include the anti-hyperlipidemic fibrate drugs. Because PPAR-alpha ligands regulate hepatic lipid metabolism, they may have utility in the treatment of steatohepatisis, or fatty liver.

PPAR-beta/delta is expressed in metabolically active tissues including skin, intestinal tract, liver, heart, skeletal muscle, lung, brain, thymus, spleen, keratinocytes and various immune cells. Its ligands includes GW1514 and retinoic acid. Agonism of PPAR-beta/delta changes the body's fuel preference from glucose to lipids, but also has been demonstrated to play a role in myelination of the corpus callosum, epidermal cell proliferation, as well as differentiation, lipid accumulation, directional sensing, polarization, and migration in keratinocytes.

PPAR-gamma is ubiquitously expressed, though mainly present in adipose tissue, colon and macrophages. Because its ligands include the thiazolidinedione (TZD) rosiglitazone, pioglitazone, troglitazone, PPAR gamma is also referred to as the "glitazone" receptor. As a regulator of adipocyte differentiation, it is important as a regulator of fatty acid storage and glucose metabolism. Compounds with activities at the PPAR-gamma site have particularly valuable pharmacologic potential as oral, injectable or otherwise systemic treatments for diabetes, insulin resistance, metabolic syndrome, obesity, atherosclerotic heart disease and other dysmetabolic states. Ligand-mediated activation of the PPAR gamma receptor is although though to be responsible for inhibiting the growth of cultured human breast, gastric, lung, prostate and other cancer cell lines (46)

Because PPARs have significant impact on anti-apoptosis and cell differentiation, anti-inflammatory activity, and lipid and glucose metabolism, embodiments of the subject invention also provide that Lf Qi6 bioextracts have particularly valuable utility as a local or systemic pharmacologic agent in a variety of disorders benefitting from PPAR agonism, including dysmetabolic, chronic inflammatory states, obesity, insulin resistance, diabetes, metabolic syndrome, atherosclerosis, steatohepatitis, Alzheimer's disease, as well as skin disorders, such as hair loss, acute and chronic wounds, diseases of chronic skin inflammation such as atopic demiatitis, rosacea, acne, sebhorrheic dermatitis, and diseases thought to involve airway neutrophilia, such as acute respiratory distress syndrome (ARDS) and chronic obstructive pulmonary disease (COPD). Treatment of metabolic disorders can include, for example, modulation of lipid, glucose and/or fatty acid storage.

In some embodiments of the current invention, the enhancement of skin barrier functions is achieved by upregulating the expression of one or more skin barrier proteins selected from, for example, filaggrin 1, filaggrin 2, loricrin, involucrin, junction proteins, and/or desmosomal proteins.

In some embodiments, the enhancement of skin innate immune functions is achieved by modulating the expression of one or more innate immune peptides and/or inflammatory cytokines, which have been associated with reduced pathogenic biofilm burden on skin surfaces.

In some embodiments, the innate immune peptides are selected from human beta defensin 1, human beta defensin 2, human beta defensin 3, human cathelicidins (LL-37), and combinations thereof.

In some embodiments, the inflammatory cytokines are selected from interleukin-1 alpha, interleukin-4, interleukin-13, thymic stromal lymphoproteins (TSLP), and combinations thereof.

Other proteins, peptides, and cytokines modulating the human skin barrier, immune, and anti-inflammatory functions will be readily recognized by the person skilled in the art.

In certain embodiments, the subject invention also provides antibacterial compositions in the form of cleaning products, washes, surface coatings or other compositions, which are not for medical treatment of the human or animal body. Thus, in specific embodiments, these compositions are used to disinfect inanimate surfaces.

In another aspect, the subject invention provides a method of treating human dermatological disorders comprising administering to a subject a therapeutically effective amount of the pharmaceutical composition, the composition preferably comprising one or more bioactive extracts of the Lf Qi6 biofilm.

"Subject", as used herein, means a human or a non-human animal, e.g., dogs, cats, mice, rats, cows, sheep, pigs, goats, non-human primates or birds, e.g., a chicken, as well as any other vertebrate or invertebrate.

Administration of the pharmaceutical compositions provided herein is preferably in a "therapeutically effective amount," this being an amount sufficient to result in a biological or medical response of a cell, tissue, system, animal, or human that is being treated. The actual amount administered, and the rate and time-course of administration, will depend on the nature and severity of the disease being treated as well as the subject. Prescription of treatment, e.g., decisions on dosage etc, is within the responsibility of general practitioners and other medical doctors, and typically takes into account the disorder to be treated, the condition of the individual patient, the site of delivery, the method of administration and other factors known to practitioners.

A composition may be administered alone or in combination with other treatments, either simultaneously or sequentially dependent upon the condition to be treated. The pharmaceutical compositions provided herein may be dissolved in, suspended in, or admixed with one or more other pharmaceutically acceptable ingredients. The compositions may also be presented in a liposome or other microparticle.

In preferred embodiments, the pharmaceutical compositions are formulated for topical administration, particularly for use or application to, or on, the skin. Such formulations may be useful for removing, killing, or preventing the adhesion and accumulation of pathogenic bacteria, such as MRSA, on a biological or non-biotic surface, or inhibiting the action or growth of the bacteria. Furthermore, in specific embodiments, compositions comprising biofilm, or the extracts thereof, of Lf Qi6 have the advantage of promoting the growth of commensal bacteria in the human skin microbiome. Non-limiting examples of the commensal bacteria include, but are not limited to, *Staphylococcus epidermidis* (*S. epidermidis*), *Staphylococcus warneri*, *Streptococcus mitis*, *Propionibacterium acnes*, *Corynebacterium* spp., *Acinetobacter johnsonii*, and *Pseudomonas aeruginosa*.

The pharmaceutical compositions provided herein may suitably be provided as a patch, adhesive plaster, bandage, dressing, or the like which is impregnated with, or coated with, the microbial biofilm and/or one or more extracts thereof and, optionally, one or more other pharmaceutically-acceptable ingredients, including, for example, penetration, permeation, and absorption enhancers.

Antibacterial compositions according to embodiments of the invention may be useful for treating biomaterials, implants and prosthesis (including stents, valves, eyes, hearing aids, gastric bands, dentures, artificial joint replacements etc.), surgical instruments or other medical devices prior to administration to, or treatment of, or use with, a subject. The antibacterial compositions may be useful for treating surfaces prone to colonization or exposure to bacteria, such as handrails, food preparation surfaces, kitchen surfaces or equipment, tables, sinks, toilets or other bathroom hardware.

Antibacterial compositions may comprise agents in addition to the microbial (e.g., Lf Qi6) biofilm or its bioactive extracts, such as cleaning agents, stabilisers, anionic surfactants, perfumes, chelating agents, acids, alkalis, buffers or detergents. Such agents may facilitate or enhance the antibacterial properties of the compositions, such as killing or inhibiting bacteria, or preventing the recolonization of the cleaned surface.

Exemplary embodiments provide that the subject is one that is affected by conditions selected from skin barrier dysfunctions, skin dysbiosis, skin innate immune dysfunctions, and combinations thereof.

Embodiments provided herein are useful in the treatment of, for example psoriasis, icthyosis, sarcoidosis, atherosclerosis, inflammatory bowel disease, acne (including hiradenitis suppurativa), dermatitis, wound healing, acne (including hiradenitis suppurativa), burns, diaper rash, Netherton's syndrome, actinic keratosis, dermatomycoses, dermatosis or ectodermal dysplasia, atopic dermatitis, contact dermatitis, sebortheic dermatitis, vulgaris, eosinophilic esophagitis, filaggrin deficiency, and/or other disorders associated with damage or breakdown of the skin barrier.

In some embodiments, repair or regeneration of the barrier includes repair or regeneration of a mucous membrane. Mucous membranes include mucosa of the mouth (including mucosa of the cheek, the soft palate, the tongue, including the under surface of the tongue and the floor of the mouth), the nose, the throat (including mucosa of the pharynx, the larynx, the trachea and the esophagus), the bronchi, the lungs, the eye, the ear, the gastrointestinal tract, the vagina, the penis, the urethra, the bladder, and the anus.

In certain embodiments, the compositions of the subject invention can also be used effectively in the treatment of acute and chronic viral infections. In particular, the treatment of chronic Epstein-Barr virus, cytomegalovirus and other herpes-type virus infection, which are ubiquitous in the population and are associated with a decrease on the immune survillance.

In a further aspect, the subject invention provides a cosmetic composition for improving human skin conditions, comprising a biologically pure strain of a bacterium and/or one or more bioactive extracts thereof, and cosmetically acceptable excipients. In preferred embodiments, the composition comprises bioactive extracts of Lf Qi6 biofilm.

"Cosmetic" as used herein is non-therapeutic. Such compositions are not directed to treating human or animal by therapy. For example, the composition may enhance the hydration level of the skin. Increased hydration level is known to improve the appearance of the skin and lead to a healthier cosmetic appearance.

In some embodiments, the cosmetically acceptable excipients comprise substances used for formulations selected from lotion, cream, emulsion, ointment, gel, serum, and combinations thereof.

Cosmetic compositions according to embodiments of the subject invention have barrier maintenance and repair activity. As such, they are useful for preventing a reduction in and/or reinforcing barrier function. This may be useful for improving hydration of the skin and/or improving the appearance of the skin.

Formulations suitable for dermal and/or transdermal administration include, but are not limited to, gels, pastes, ointments, creams, lotions, and oils, as well as patches, adhesive plasters, bandages, dressings, depots, cements, glues, and reservoirs.

Ointments are typically prepared from the cosmetic compositions provided herein and a paraffinic or a water-miscible ointment base.

Creams are typically prepared from the cosmetic compositions provided herein and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

As would be readily appreciated by one skilled in the art, formulations according to the subject invention could also comprise other alcohols, such as, for example, isopropyl alcohol or ethanol, and could also cover other alcohol based formulations, for example alcohol based hand sanitizers.

The topical formulations may desirably include a compound that enhances absorption or penetration of the active compound through the skin or other affected areas. Examples of such dermal penetration enhancers include dimethylsulfoxide and related analogues.

Emulsions are typically prepared from the cosmetic compositions provided herein and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low.

Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used. Other formulations include dental sprays, mouthwashes, toothpastes, lozenges, antibacterial washes, drinks (e.g., milk, yoghurt), food items (such as yoghurt, ice cream, candy bars), or powdered foods (such as powdered milk).

In some embodiments, the cosmetic composition has biological activities selected from inhibiting pathogenic biofilm growth, inhibiting pathogenic biofilm adhesion, promoting pathogenic biofilm detachment, promoting commensal biofilm growth, enhancing skin barrier functions, enhancing skin innate immune functions, and combinations thereof.

In yet another aspect, the subject invention provides a method of improving human skin conditions, comprising administering to a subject a cosmetically effective amount of a composition comprising a biologically pure bacterial strain, and/or one or more bioactive extracts thereof, and cosmetically acceptable excipients, the bacterial strain and its extract being capable of growing in both planktonic and biofilm phenotypes, the composition having biological activities selected from inhibiting pathogenic biofilm growth, inhibiting pathogenic biofilm adhesion, promoting pathogenic biofilm detachment, promoting commensal biofilm growth, enhancing skin barrier functions, enhancing skin innate immune functions, and combinations thereof. In preferred embodiments, the bacterial strain is Lf Qi6.

The cosmetic treatment may be used to improve the appearance and/or texture of the skin. In an exemplary embodiment, the method relates to improving the hydration level, or appearance, of the skin. As used herein the term "cosmetic method" does not refer to a method for treatment of the human or animal body by surgery or therapy, or diagnostic methods practiced on the human or animal body.

The subject to be treated may be any animal or human. The subject may be a non-human mammal, but is more preferably a human. The subject may be male or female. In some embodiments, the subject does not require repair of his or her skin barrier, or to be treated for infection, such as bacterial infection. In some embodiments, the subject does not require treatment at the site at which the cosmetic treatment is to be applied.

The cosmetic methods according to the invention preferably involve the administration of a "cosmetically effective amount". This pertains to the administration of compounds, ingredients, materials, compositions, dosage forms, etc. in an amount effective to induce a cosmetic benefit. This is within the scope of sound judgement of a relevant practitioner. It will be appreciated by one of skill in the art that appropriate dosages of the active compounds, and compositions comprising the active compounds, can vary from subject to subject.

The pharmaceutical or cosmetic compositions provided herein may contain a single (unit) dose of probiotic bacteria, or lysate, or extract thereof. Suitable doses of probiotic bacteria (intact, lysed or extracted) may be in the range $10^4$ to 1012 cfu, e.g., one of 104 to 1010, 104 to 108, 106 to 1012, 106 to 1010, or 106 to 108 cfu. In some embodiments, doses may be administered once or twice daily. In some embodiments, a composition for use according to the present invention may comprise at least about 0.01%, about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0% by weight of the Lf Qi6 extracts. In some embodiments, the compositions may comprise, one of at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to 10 about 5%, by weight of the Lf Qi6 extracts.

For the purpose of the present invention the abbreviation cfu shall designate a "colony forming unit" that is defined as the number of bacterial cells as revealed by microbiological counts on agar plates.

All patents, patent applications, provisional applications, and publications referred to or cited herein are incorporated by reference in their entirety, including all figures and tables, to the extent they are not inconsistent with the explicit teachings of this specification.

Materials and Methods

Bacterial Strains and Culture Media

Methicillin-resistant *Staphylococcus aureus* (MRSA) ATCC 33591 (ATCC, Manassas, Va.) was stored in tryptone soya broth (TSB) (Thermo Scientific, Waltham, Mass.) containing 20% (v/v) glycerol at −80° C. Culture was incubated overnight at 37° C., aerobic, on a rotary shaker at 110 rpm. Optical density of the overnight culture was read with spectrophotometer (SpectraMax Plus384, Molecular Devices, Sunnyvale, Calif.) and diluted to $0.2OD_{600}$. The strain was also subjected to both met and eap PCR using established protocols to confirm MRSA status (23). *Lactobacillus fermentum* Qi6 (Lf Qi6) was grown in MRS media at 37° C. Lf Qi6 is a proprietary strain. The genome of this strain is sequenced (GenBank Accession No. LAIK00000000). The descriptions of the Lf Qi6 genome sequence are incorporated by reference in their entirety (24), and specifically included therein is the web access to the whole genome sequence from http://www.ncbi.nlmnih.gov/nuccore/LAIK00000000. *Staphylococcus epidermidis* K7 was isolated and identified from human microbiota, and the commensal nature of the strain is verified using standard PCR tests for mecA, fdh, esp, eap genes (25-26).

Culture of Lf Qi6 Biofilm

FIG. 1 shows procedures for seeding the Lf Qi6 culture. After being isolated and identified, Lf Qi6 was cultured in MRS agar plate. The culture was then incubated in 5 ml of MRS broth for 24 hour at 37° C. 1 ml of the culture was transferred into a T-150 tissue culture plate with 25 ml of MRS broth. 25 ml of MRS media was changed every 48 hours to allow the biofilm of Lf Qi6 to grow as lawn on the bottom of the culture plate. The culture was then grown for 7 days to produce a thick biofilm layer. The grown biofilm layer was subsequently scraped out and suspended in fresh medium. Freezer stacks were made with glycerol and stored in −80°.

Figure 4:
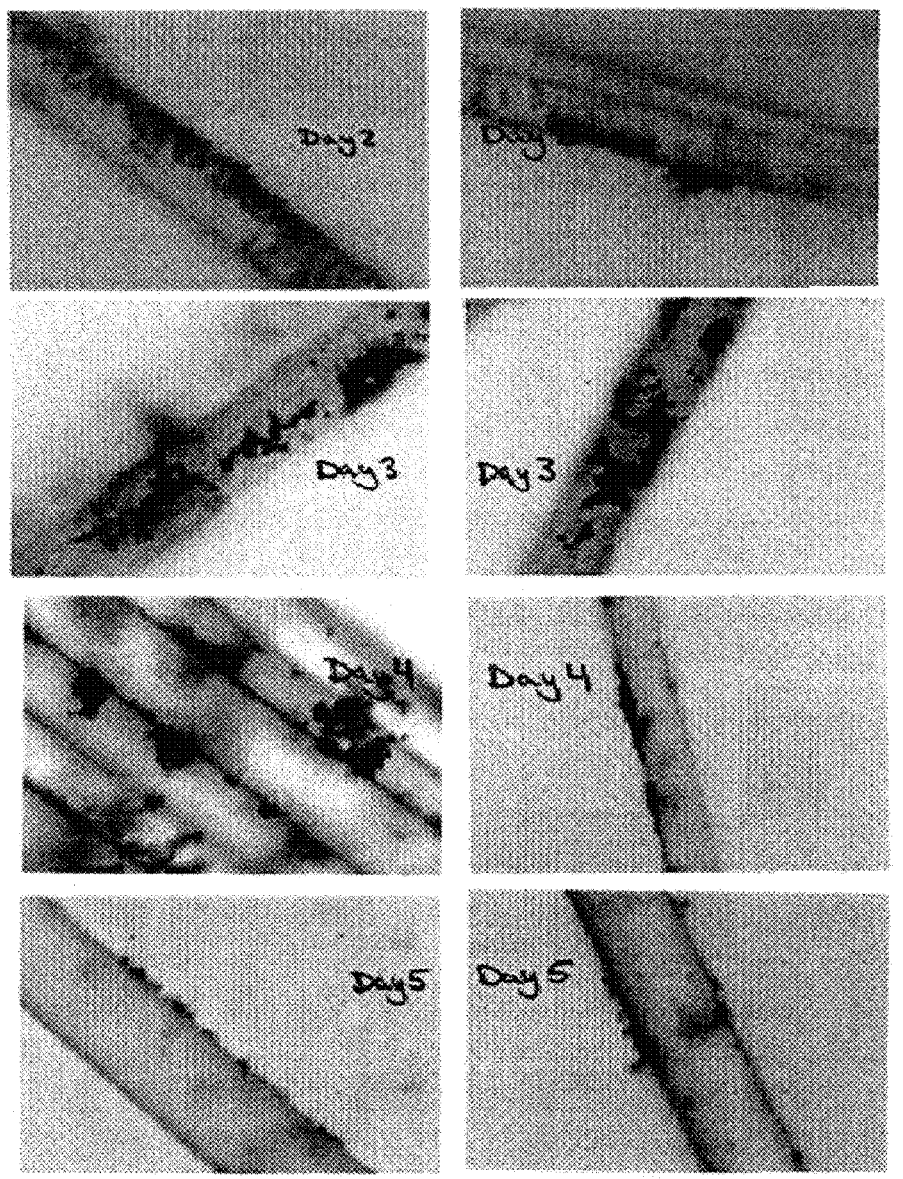
FIG. 4 illustrates biofilm growth of Lf Qi6 in substrates in scale-up culture.

A scaled-up production of Lf Qi6 biofilm is illustrated in FIG. 2. A biofilm phenotype of Lf Qi6 in frozen stock was cultured in 10 ml of fresh MRS media for 24 hour at 37°. 10 ml of culture was inoculated into 25 L of MRS media with 500 g sterile glass wool. The biofilm was then cultured for 72 hours under static conditions at 37° C. The culture was mixed every 24 hours with a gentle shaking, after which the media and glass wool were harvested. The biofilm cells were subsequently detached from the glass wool via sonication. The cells were further centrifuged to concentrate the biofilm of Lf Qi6, which was then suspended in sterile water. This scale-up yields a biofilm culture at a concentration of 50 g/25 L. The Lf Qi6 biofilm growth is further illustrated in FIG. 4, wherein the biofilm was cultured on substrates in a scaled-up culture as described herein.

Lf Qi6 Biofilm Downstream Processing

The downstream processing of Lf Qi6 biofilm is shown in FIG. 3. 50 g of biofilm phenotype of Lf Qi6 was suspended in 1 L of sterile water. The suspension was gently mixed for 24 hours at room temperature to allow the passive release of multiple bioactives. The mixture was then sonicated for 30 minutes (50 KHz, 200 watt) into uniform lysate using an OmniSonic Ruptor 400. The sonicated lysate was then frozen and lyophilized into a fine powder.

Culture of Human Keratinocyte Cell Line

HEKa cells were purchased from Life Technologies (Grand Island, N.Y., USA Cat# C-005-5C). HEKa cells were maintained in Medium 154 (Life Technologies, Grand Island, N.Y., USA Cat#M-154-500) supplemented with Human Keratinocyte Growth Supplement (Cat#S-001-5).

Human Ex-Vivo Organotypic Culture

Surgical specimens of human skin were obtained post-cosmetic surgery. All samples were obtained from patients who gave informed consent to use excess skin specimens for research purposes. Skin was transported to the laboratory in fresh Eagle's minimum essential medium (EMEM) with L-glutamine (AFCC, Manassas, Va.) supplemented with 1% antibiotic-antimycotic solution (penicillin, streptomycin, amphotericin) (Hyclone, Thermo Scientific, Logan, Utah). The medium and skin were stored at 4° C. prior to cutting). Culture medium was composed of Keratinocyte-complete serum free medium supplemented with human recombinant Epidermal Growth Factor (0.2 ng/ml EGF), Bovine Pituitary Extract (30 µg/ml BPE) (Life technologies, Grand Island, N.Y.), and 1% antibiotic-antimycotic solution. 6-well plates were prepared with 1.3 ml culture medium and one Milli-cell-CM cell culture insert (0.4 µm, 30 mm diameter) (EMD Millipore, Billerica, Mass.) per well. Explant samples were prepared for cutting by washing gently in fresh supplemented EMEM in a sterile petri dish. Explants were moved with sterile forceps to a fresh dish containing EMEM, cut into 1 $cm^2$ pieces using sterile surgical scissors and placed over cell culture inserts in 6-well plates so the underside portions of the skin were exposed to air (air-liquid interface). Explants were cultured at air-liquid interface on cell culture inserts at 37° C. with 5% $CO_2$ for 5-7 days, based on experimental protocol, with medium changed daily.

Preparation of Lf Qi6 from Probiotic Bacteria

*L. fermentum* Qi6 was grown in MRS media using proprietary culture methods. Bacteria were then subcultured into 500 ml MRS medium for an additional period, again using proprietary culture methods. Bacteria were sonicated (Reliance Sonic 550, STERIS Corporation, Mentor, Ohio, USA), centrifuged at 10,000 g, cell pellets dispersed in sterile water, harvested cells lysed (Sonic Ruptor 400, OMNI International, Kennesaw, Ga., USA) and centrifuged again at 10,000 g, and soluble fraction centrifuged (50 kDa Amicon Ultra membrane filter, EMD Millipore Corporation, Darmstadt, Germany, Cat#UFC905008). The resulting fraction was distributed into 0.5 ml aliquots, flash frozen in liquid nitrogen and stored at −80° C.

Biofilm Inhibition Assay

MRSA was added to the wells of sterile polystyrene, tissue-culture (TC) treated, flat-bottom plates (Genesee Scientific, San Diego, Calif., Cat #25-109). TSB served as sterility control. Growth control wells received equal parts MRSA and culture medium. Chosen concentrations of Lf Qi601 or other test agents were added, the plate incubated at 37° C. for 18 h and then biofilm quantified as described in the staining and biofilm quantification section.

Biofilm Detachment Assay

MRSA was added to the wells of a sterile TC plate and incubated at 37° C. for 18 hr. The plate was washed three times with 1× phosphate buffered saline (PBS) (Thermo Scientific, Waltham, Mass.) using BioTek 405 Select LS Microplate Washer (BioTek, Winooski, Vt.). Fresh TSB was added to each well. Chosen concentrations of Lf Qi6 were added, then the plate placed in the incubator at 37° C. for 10 min. Remaining biofilm was stained and quantified as described below.

Anti-Biofilm Adhesion Assay

Wells of a TC plate were coated with chosen concentrations of Lf Qi6 or other test agents; growth control and negative control wells received PBS, and incubated overnight at 4° C. static. Plates were washed three times with PBS using BioTek microplate washer. After washing, MRSA was added, and the plate incubated at 4° C. for 5 h. Adhered biofilm was stained and quantified.

Staining and Biofilm Quantification

The plate was washed three times with PBS using the BioTek plate washer and placed in a 47° C. incubator for one hour to heat-fix biofilm. The plate was cooled to room temperature, stained with 0.1% (v/v) crystal violet for 15 min, then washed with deionized $H_2O$ using the microplate washer. 100% ethanol was added for 30 min in order to dissolve crystal violet stain. The plate was read at 590 nm and 600 nm using a spectrophotometer (SpectraMax Plus384, Molecular Devices, Sunnyvale, Calif.).

Ex Vivo Skin Biofilm Studies

Histological Examinations of biofilms in ex vivo skins were confirmed using the Hematoxylin-Eosin Staining protocol developed by Hochstim et al. (2010) (27). Ex vivo skin cultures were treated with chosen concentrations of Lf Qi6, inoculated with 100 μl of either low or high density MRSA cultures, and grown overnight. Skin tissues were then homogenized, diluted, and cultured on TSB plates to quantify colony forming units (CFUs) per sample.

In Vitro Pathogenic and Commensal Co-Culture Studies

Six-well plates were treated with Lf Qi6 or bacterial cultures for 5 h. MRSA and S. epidermidis K7 inoculum of identical optical densities (ODs) were prepared in TSB. Two mls of these mixtures were inoculated in triplicate in treated vs control wells of 6-well plates.

Ex Vivo Pathogenic and Commensal Co-Culture Studies on Human Skin Explants

Skin explants surfaces were treated with Lf Qi6, the chemical detergent 0.2% Triton as positive control, or PBS as negative control, and incubated overnight at 37° C. at 5% $CO_2$. MRSA and K7 cultures of identical optical densities were prepared in TSB. The skin surface was inoculated with 50 μl of each bacterial culture and incubated overnight at 37° C. Skin tissues were then homogenized, diluted, and cultured on TSB and ORSAB plates to quantify and differentiate pathogenic vs. commensal CFU's per tissue.

Filaggrin ELISA

A human filaggrin ELISA kit (EIAab, Wuhan, China, Cat#1186h) was used to quantify filaggrin. Treated skin explant tissues were homogenized with 1 ml PBS mixed with protease inhibitor cocktail (Thermo Scientific, Product #78425), and frozen overnight at −20° C. Samples were then subjected to two freeze thaw cycles to break cell membranes. Homogenates were centrifuged at 10000×g for 5 min. Supernatant was aliquoted and stored at −20° C./−80° C. for 2-5 days. Manufacturer's directions were followed to quantify levels of filaggrin in homogenates of the skin explant. The assay was performed in triplicate/sample condition. ELISA results were analyzed on Molecular Device's SpectraMax Plus384 using SoftMax® Pro software (Molecular Devices, Sunnyvale, Calif., USA). Statistical analysis was performed using GraphPad Prism version 6.03 (GraphPad Software, Inc., La Jolla, Calif., USA).

Immunohistochemistry

Morphological and immunofluorescent analyses were performed on 5 μm paraffin-embedded NEM sections. For analysis of morphology, skin explants were fixed in 10% formalin, sectioned, deparaffinized, rehydrated and stained with hematoxylin and eosin (HE). For analysis of filaggrin expression, sections were cut, deparaffinized and rehydrated, followed by heat-mediated antigen retrieval. After blocking non-specific binding using PBS containing 1% bovine serum albumin (BSA, Sigma) and 2% normal human serum (NHS, Sanquin, Leiden, the Netherlands), the sections were incubated overnight at 4° C. with primary antibody for filaggrin (1:1000; Covance, Rotterdam, the Netherlands). After washing with PBS, sections were incubated with secondary goat antibody anti-rabbit (Rhodamine Red, 1:300, Jackson Immuno Research, Amsterdam, the Netherlands). Sections were then incubated with streptavidin peroxidase for 10 min. at room temperature and rinsed with buffer 4 times. DAB chromogen was added to sections to visualize staining for 5 min. Slides were counterstained with hematoxylin solution for 1 min. Negative control was prepared without addition of antibody. Isotype controls were also included in the protocol. The sections were mounted with Vectashield containing DAPI for visualization of the nuclei (Vector Laboratories, Amsterdam, the Netherlands). Quantitative Immunoratio analysis from various 8-9 fields from immunostained slides were done by modifying the protocol developed by Tuominen et al (2010) (28).

RNA Isolation, cDNA Synthesis and qPCR Analysis

Tissue explants for qRT-PCR were flash frozen in liquid nitrogen. Total RNA was isolated and purified using RNAqueous-4PCR kit (Ambion) according to manufacturer's instructions and stored at −80° C. until reverse transcription. For real-time PCR analysis, cDNA was synthesized from 0.1 μg of total RNA using high capacity cDNA Reverse Transcription kit (Applied Biosystems, Foster City, Calif.) according to manufacturer's instructions. Quantitative PCR was performed using Power SYBR Green PCR master mix on a 7500 Real-Time PCR system (Applied Biosystems). Primers were chosen from the literature (Table. S1) and obtained from IDT technologies. Cycling conditions were as follows: 2 mins at 50° C., 10 mins at 95° C., and 40 cycles of 15 sec at 95° C. and 1 min at 60° C. Reaction was followed by a dissociation step and melting curves were assessed for primer specificity. PCR for each template was performed in triplicate in 96-well plates. The mRNA expression levels were normalized to β-microglobulin reference gene using the comparative CT (ddCT) method with Data Assist™ software (Applied Biosystems). Negative control reactions without template were included for each primer combination.

Statistical Analysis

Quantitative data of various parameters are presented as the mean±SEM (standard error of means) in figures. Statistically significant differences in various parameters were determined by one-way ANOVA test. When significant differences (P≤0.05) existed, the means were compared using the Newman-Keuls multiple comparison test. Statistical software GraphPad Prism (GraphPad Software, Inc., San Diego, Calif.) was used to perform statistical analyses.

Our qRT-PCR results showed approximately 250 fold upregulation in filaggrin in skin treated with bioextract compared to PBS baseline. We confirm the increased filaggrin protein production via ELISA and immunohistochemistry.

Following are examples that illustrate procedures for practicing the invention. These examples should not be construed as limiting.

EXAMPLE 1

Lf Qi6 Biofilm Phenotype Differs from the Planktonic Phenotype

Figure 5:
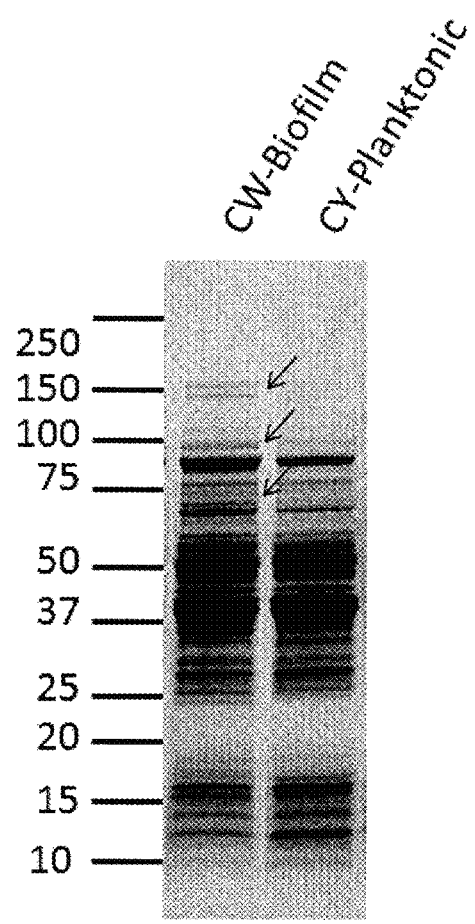
FIG. 5 illustrates SDS bands showing unique proteins in bioextract prepared from Lf Qi6 biofilm phenotype. Arrows show unique proteins in biofilm phenotype compared to planktonic phenotype.
Figure 6:
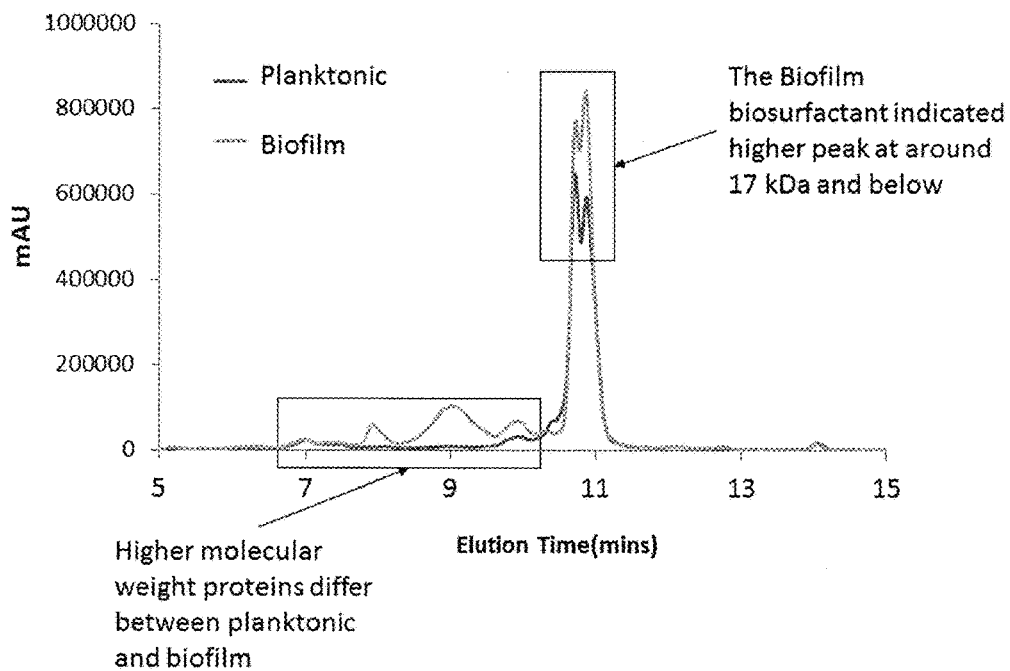
FIG. 6 illustrates size-exclusion HPLC showing unique proteins in bioextract prepared from Lf Qi6 biofilm phenotype.
Figure 7:
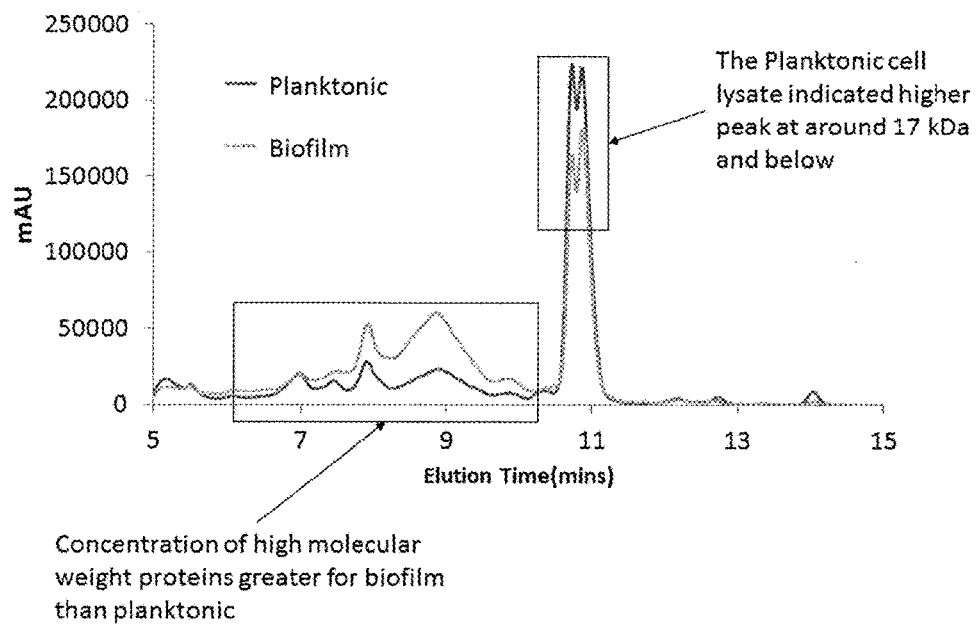
FIG. 7 illustrates size-exclusion HPLC showing unique proteins in bioextract prepared from Lf Qi6 biofilm phenotype.

Product extraction and protein estimation demonstrate different protein levels between the biofilm and planktonic phenotypes, as seen in Table 1 below. SDS data in FIG. 5 further corroborate such differences, as shown by extra bands expressed in the Lf Qi6 biofilm phenotype that are not present in the planktonic phenotype, indicative of unique proteins in the bioextract of the biolfilm. Size-exclusion HPLC data in FIGS. 6 and 7 illustrate differences in molecular weight between proteins in bioextract prepared from Lf Qi6 biofilm and planktonic phenotype.

TABLE 1

Product extraction and protein estimation from biofilm and planktonic shows different protein levels.

|  | Sample No. | Description | Extract Yield (g/L) | Protein Yield (g/L) | Protein % In Extract |
|---|---|---|---|---|---|
| Pellet | 1 | Planktonic | 0.4 | 0.2 | 52.2 |
|  | 2 | Biofilm-unextracted | 0.7 | 0.4 | 61.3 |
|  | 3 | Biofilm-extracted | 0.6 | 0.2 | 37.3 |
| Cell Lysate | 1 | Planktonic | 0.09 | 0.03 | 30.8 |
|  | 3 | Biofilm-extracted | 0.10 | 0.04 | 34.7 |
|  | 4 | Biofilm-unextracted | 0.2 | 0.06 | 31.6 |
| Biosurfactant | 1 | Planktonic | 0.12 | 0.05 | 42.2 |
|  | 3 | Biofilm-extracted | 0.16 | 0.06 | 36.7 |

Figure 8:
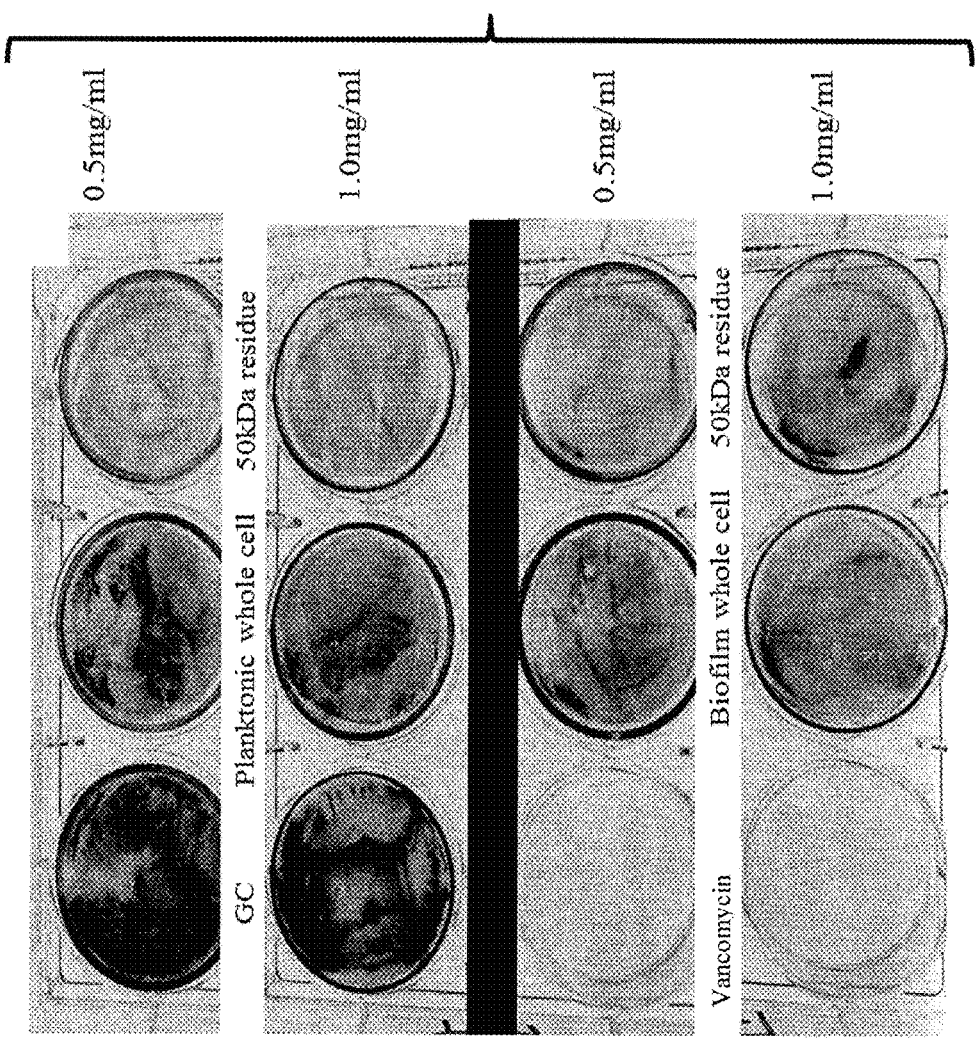
FIG. 8 illustrates Lf Qi6 biofilm extracts having high anti-biofilm activity against MRSA.
Figure 9:
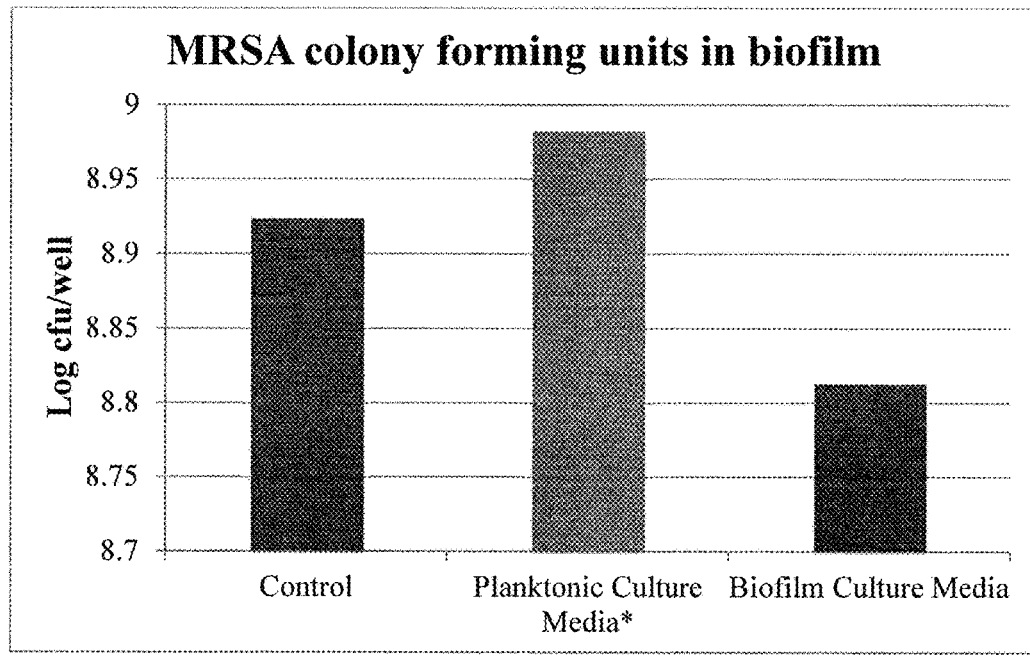
FIG. 9 illustrates MRSA colony forming units in biofilm.

The anti-biofilm activity against MRSA was evaluated between the Lf Qi6 biofilm and planktonic phenotypes in 6-well plates, as shown in FIG. 8, with the negative control being a GC-rich culture of MRSA grown in TSB and the positive control being an MRSA-biofilm treated with vancomycin. The MRSA culture was inoculated with 0.5% glucose and incubated overnight at 37° C. The Lf Qi6, at 0.5 mg/mL and 1.0 mg/mL, respectively, in both planktonic or biofilm whole cells phenotypes, was pre-coated in each well for 2 hours at 4° C. Included in the observation was >50 kDa residue of spent Lf Qi6 cultures at two different concentrations for each phenotype. It is evident that the extracts of the Lf Qi6 biofilm phenotype demonstrated inhibition of MRSA biofilm growth at both 0.5 and 1.0 mg/mL. These results were quantified and presented in FIG. 9, wherein the colony forming units of MRSA were significantly reduced by the Lf Qi6 biofilm culture medium as compared to both the control and the planktonic culture medium.

Figure 10:
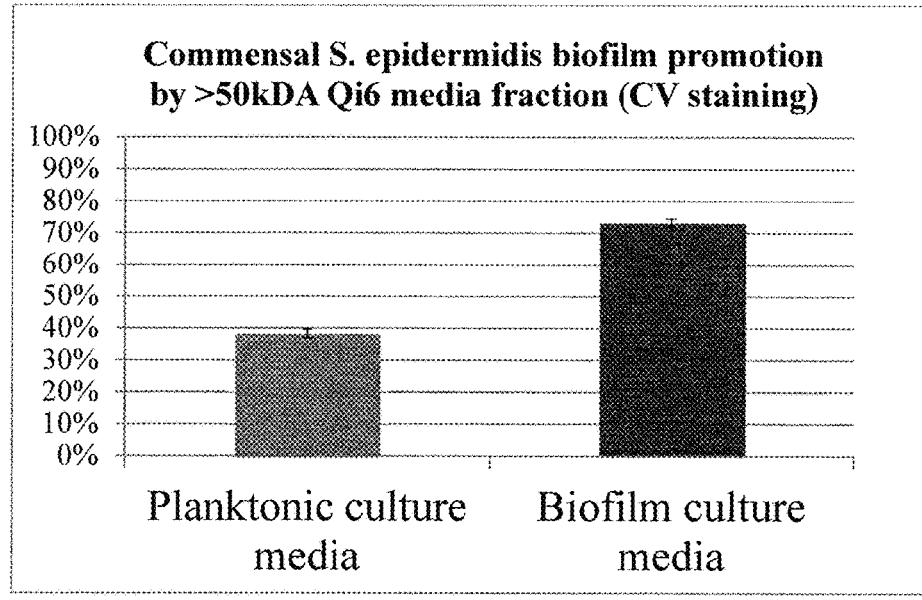
FIG. 10 illustrates commensal *S. epidermidis* biofilm promotion by >50 kDA Qi6 media fraction (CV staining).
Figure 11:
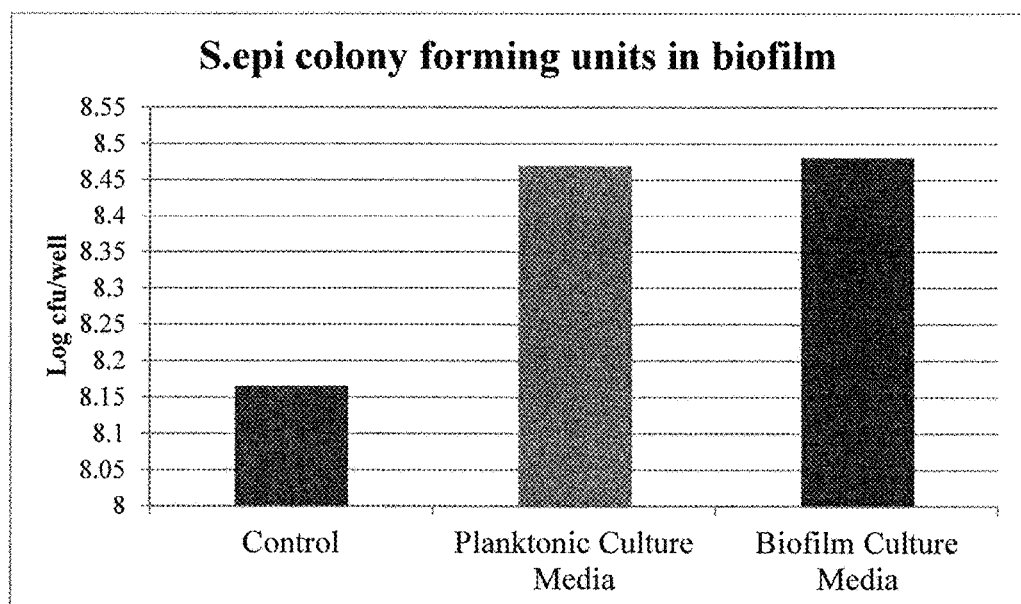
FIG. 11 illustrates *S. epidermidis* colony forming units in biofilm.
Figure 12:
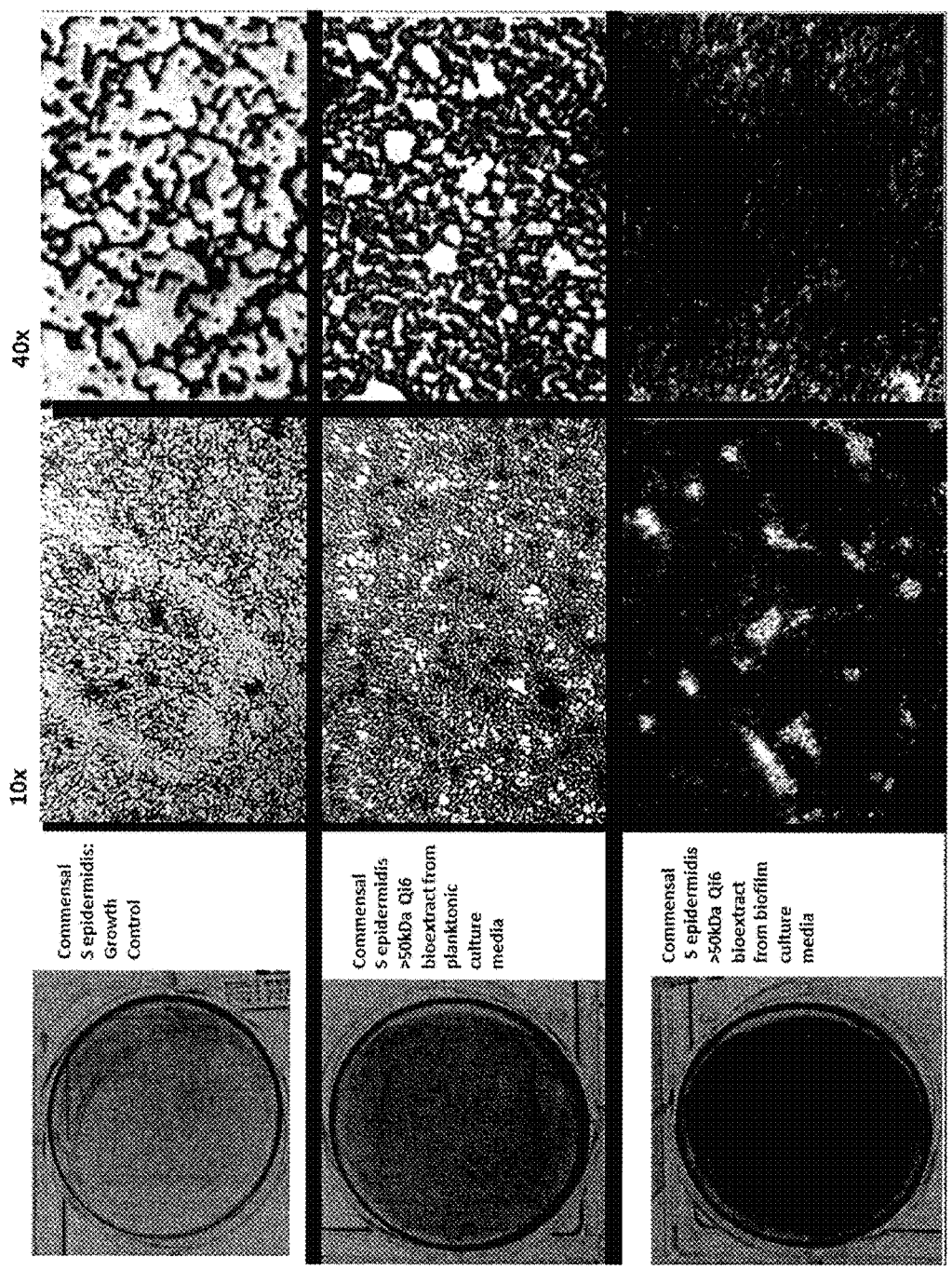
FIG. 12 illustrates commensal *S. epidermidis* growth control.

The promotion of commensal bacteria *S. epidermidis* by Lf Qi6 media fraction (>50 kDa of extract) was evaluated for both the planktonic and the biofilm culture medium (FIG. 10). The result clearly demonstrates the advantage of the biofilm medium at enhancing the growth of *S. epidermidis* at greater than 70%, while the planktonic phenotype was only less than 40% effective in such promotion of commensal biofilm growth. Quantitative colony forming units for *S. epidermidis* in the presence of the Lf Qi6 biofilm and planktonic culture medium are compared in a chart shown in FIG. 11. Furthermore, FIG. 12 shows the results of a visual comparison between the control (i.e., *S. epidermidis* growth culture), *S. epidermidis* with Lf Qi6 bioextract (>50 kDa) from planktonic culture medium, and *S. epidermidis* with Lf Qi6 bioextract (>50 kDa) from biofilm culture medium.

EXAMPLE 2

Figure 19C:
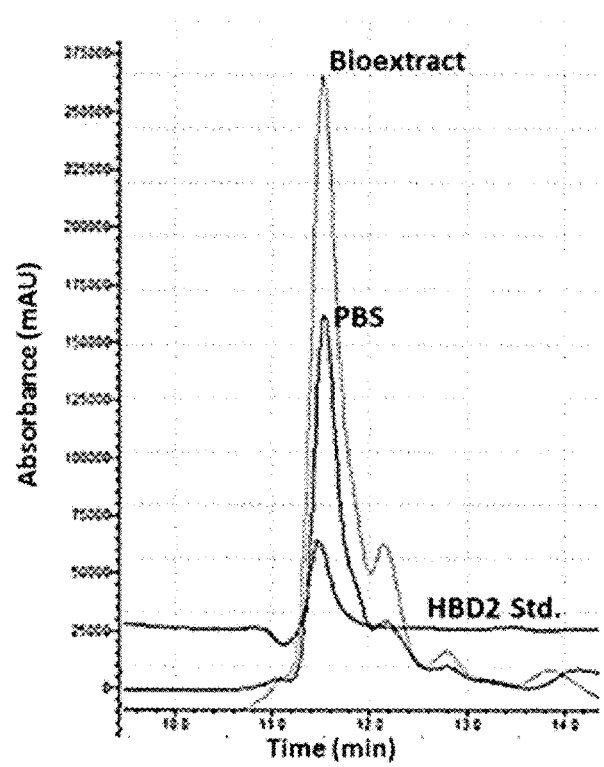
FIG. 19C shows the identification of beta-defensin 2 via HPLC from tissue culture media treated with LfQi6 bioextracts. Data is represented as the mean±SEM (standard error of means) and one-way ANOVA was used to determine differences among treatment means ($P < 0.05$). *** denotes $P<0.001$.

Lf Qi6 Biofilm has Anti-Biofilm Activities Against MRSA In Vitro: Inhibition, Anti-Adhesion, and Detachment Various anti-biofilm activities of Lf Qi6 were initially assessed in vitro via 96-well plate assays, including inhibition, anti-adhesion and detachment. The biofilm inhibition assay evaluates the new biofilm forming capacity of MRSA when co-incubated with Lf Qi6. Results demonstrate that Lf Qi6 at 0.5-1.0 mg/mL inhibits 40-50% of MRSA biofilm formation measured at 24-hour co-incubation (FIG. 19A). The anti-adhesion assay evaluates the ability of Lf Qi6 to prevent MRSA from binding to a surface. Overnight pre-treatment with 0.5-1.0 mg/ml Lf Qi6 followed by a 5-hour MRSA biofilm exposure blocked 80-85% MRSA biofilm adhesion in a 24-hour culture assay (FIG. 19B). The biofilm detachment assay demonstrates the ability of Lf Qi6 to remove a preformed biofilm; at 5 minutes of treatment, 0.5-1.0 mg/mL of Lf Qi6 detached 30% of MRSA biofilm (FIG. 19C), with similar results obtained in a larger format tissue culture plate (6-well plate, 8.5 cm$^2$ FIG. 19D).

EXAMPLE 3

Lf Qi6 Rapidly Detaches MRSA Biofilm in an Ex Vivo Human Skin Organotypic Culture System An ex vivo organotypic human skin culture system was optimized for the purpose of biofilm inoculation onto living human skin explants obtained from surgical specimens. MRSA biofilm cultures were inoculated onto the ex vivo surface and allowed to grow for 48 hours. Biofilm was visualized via stain, with robust biofilms forming on the skin in 24 to 48 hours (FIG. 19E). Comparing pre- with post-treatment, a significant reduction in MRSA biofilm burden was noted at 10 minutes of treatment with 0.5-1.0 mg/mL of Lf Qi6 (FIG. 13).

EXAMPLE 4

Lf Qi6 Selectively Enhances *S. epidermidis* while Reducing MRSA In Vitro and on Ex Vivo Skin The preliminary studies on biofilm modulating characteristics of Lf Qi6 were studied in a 6-well pathogen-commensal co-culture model using MRSA and *S. epidermidis*. Results indicate that Lf Qi6 applied at 0.5-1.0 mg/mL reduces MRSA biofilm pathogen burden while promoting commensal bacteria (FIG. 14A), with similar results in an ex vivo human organotypic culture system (FIG. 14B).

EXAMPLE 5

Figure 15A:
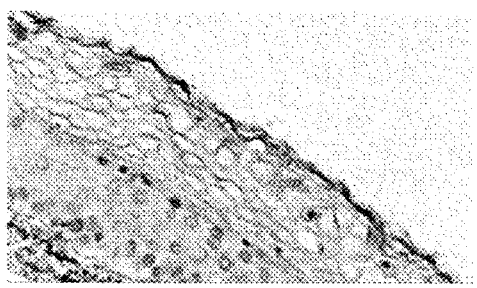
FIGS. 15A-15F illustrate the expression of skin barrier protein filaggrin (FLG) in keratinocytes upregulated by bioextracts from Lf Qi6.
Figure 15B:
Figure 15C:
Figure 15D:
Figure 15E:
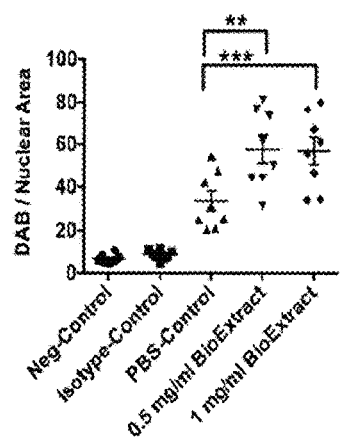
Figure 15F:
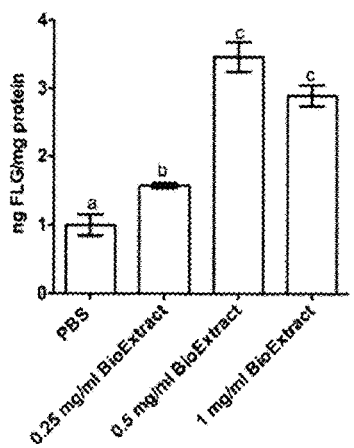

Lf Qi6 Upregulates the Skin Barrier Homeostatic Protein, Filaggrin, at RNA Expression and at Protein Level, and Significantly Increases Filaggrin Immunohistochemical Staining in an Ex Vivo Human Organotypic Culture System Filaggrin immunohistochemistry shows significantly increased staining for filaggrin protein on the epidermis of samples from the ex vivo human organotypic culture system treated with 0.5-1 mg/ml application of Lf Qi6 for a 6-hour period (FIGS. 15A-D). Lf Qi6-treated ex-vivo skin shows an approximately 3-fold increase in filaggrin protein using ELISA (FIG. 15E), as well as an approximately 250-fold increase in RNA expression using quantitative PCR (FIG. 15F).

EXAMPLE 6

Lf Qi6 Increases Expression of the Host Innate Immune Defense Peptides, Human Beta Defensin-1, Human Beta Defensing-2, and Human Beta Defensin-3

FIG. 18 compares the increases in the expression of human beta defensins 1, 2, and 3 in the presence of Lf Qi6 biofilm culture at various concentrations, namely 0%, 0.03%, and 0.10%, respectively, in an HEK cell model processed by ELISA (FIG. 18). The results demonstrated a dose-dependent effect on the expression of the aforementioned beta defensins as well as differences in the overall effect of Lf Qi6 on each characteristic beta defensing.

Furthermore, host innate immune anti-microbial peptides are integral components of skin defense system. Quantitative PCR results showed approximately 800-fold upregulation in HβD-2 (FIG. 19A) and HβD-3 (FIG. 19B) in skin treated with Lf Qi6 biofilm versus the control.

EXAMPLE 7

Lf Qi6 Biofilm Modulates Peroxisome Proliferator-Activated Receptors (PPARs)

Figure 16:
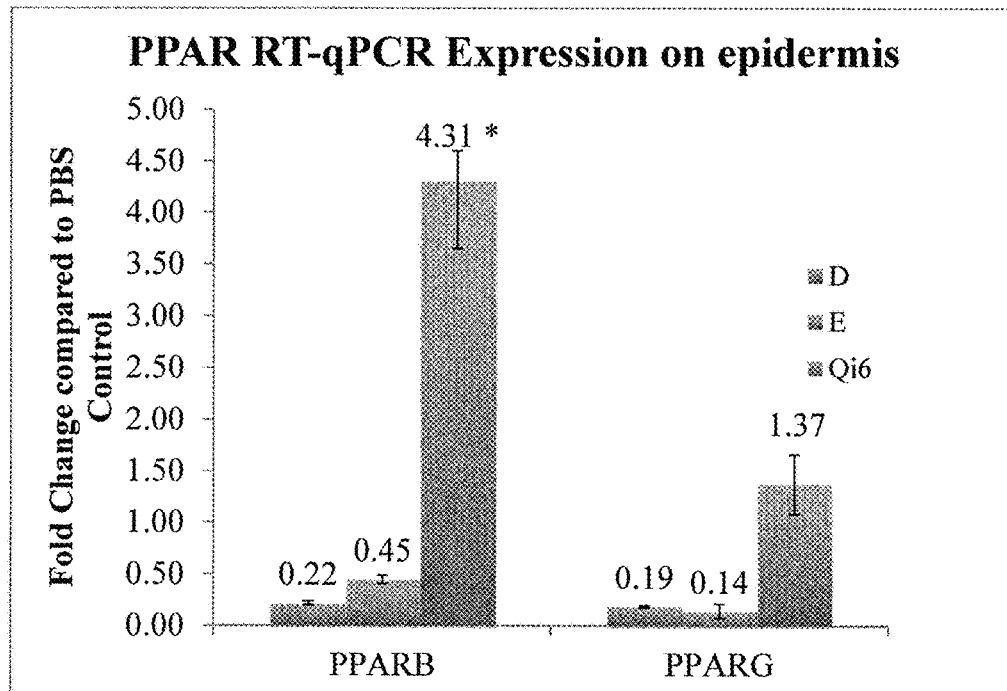
FIG. 16 illustrates that Lf Qi6 bioactives increase PPAR beta, and gamma in keratinocytes.
Figure 17:
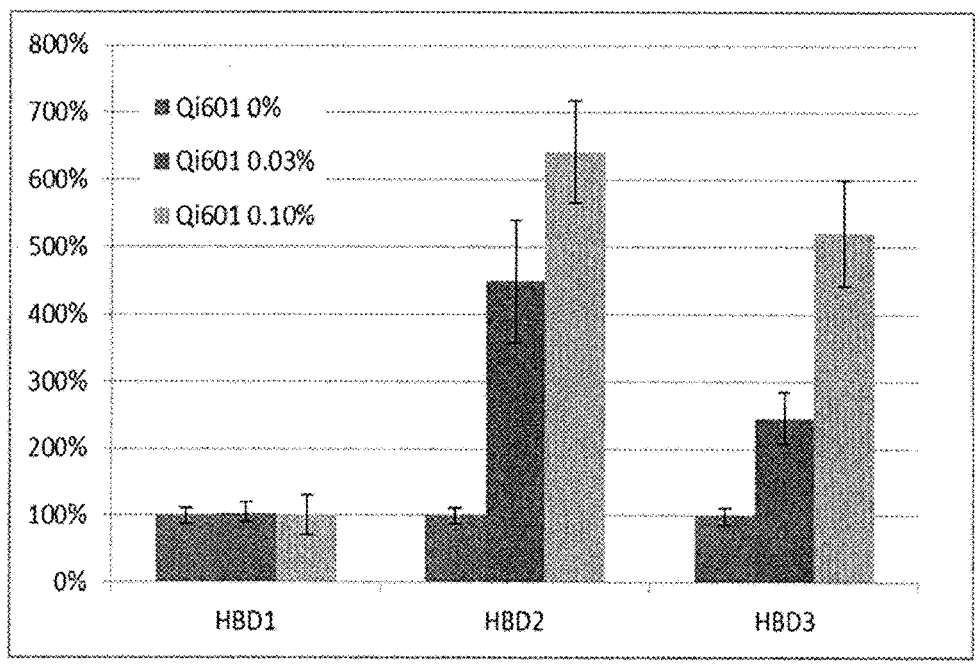
FIG. 17 illustrates that LFQi507 increases expression of human beta defensins.
Figure 18A:
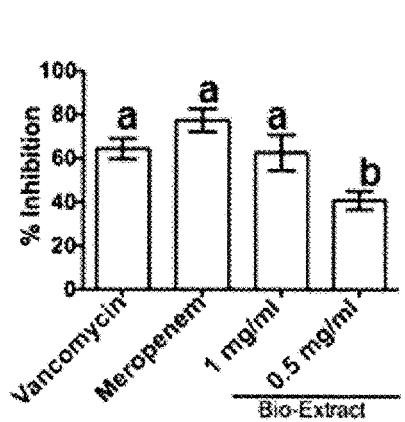
FIG. 18A shows the percent MRSA biofilm inhibition by Lf Qi6 bioextracts compared to vancomycin and meropenem.
Figure 18B:
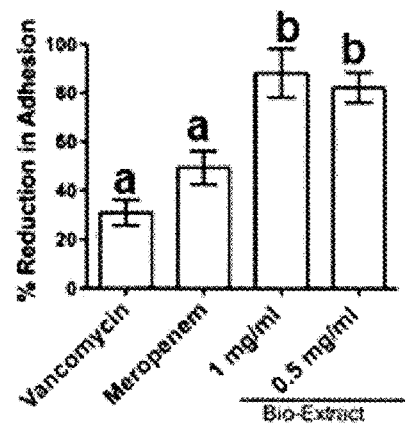
FIG. 18B shows the percent reduction in MRSA biofilm adhesion by Lf Qi6 bioextracts compared to vancomycin and meropenem.
Figure 18C:
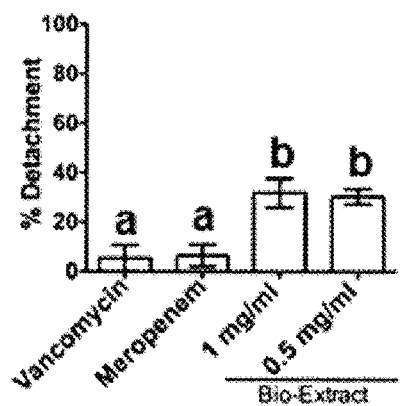
FIG. 18C shows the percent MRSA biofilm detachment following the treatment of vancomycin, meropenem, or Lf Qi6 bioextracts.
Figure 18D:
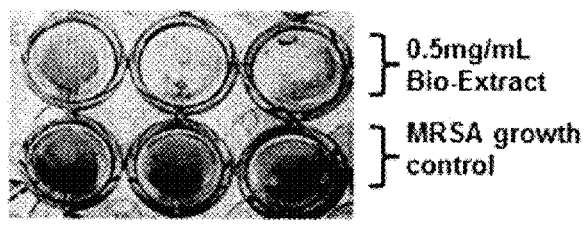
FIG. 18D shows the inhibition of MRSA biofilm treated with Lf Qi6 bioextract in a 6-well plate with coomassie biofilm staining

Since LfQi6 increases filaggrin production and filaggrin is a transcription product of PPAR-alpha, LfQi6 extracts were investigated regarding their ability to stimulate PPAR nuclear receptors. Bioactives of Lf Qi6 biofilm extraction have been shown to increase the expression of PPAR-beta and PPAR-gamma in keratinocytes as shown in FIG. 16. In particular, a small molecular size fractionated extract (<30 kD fraction, generated by differential centrifugation of the whole extract for a particular time using a specific filter for <30 kD, e.g., Amicon Ultra-15, 30K NMWL, cat# UFC 903096; extract centrifuged @ 4,000 rpm×45 minutes) appeared to have more potent activity than unfractionated LfQi601 extracts.

EXAMPLE 8

Lf Qi6 Biofilm can be Used as an Active Ingredient in a Variety of Moisturizing Skin-Care Products Lf Qi6 biofilm extracts can be used as an active ingredient in a variety of products aimed to improve the physical and biochemical functional properties of skin barrier. For example, Lf Qi6 biofilm extracts can be used to reduce transepidermal water loss and, in turn, improves skin hydration. The following exemplary formulations are directed to a variety of skin-care products including face lotion, eye cream, serum, and face wash. Each ingredient is presented in percent composition with its trade/brand name and international nomenclature of cosmetic ingredients (INCI) name, respectively. Typical properties and methods of preparing each formulation are also included.

TABLE 2

| Face lotion formulation comprising Lf Qi6 bioextracts ||||
|---|---|---|---|
| Trade/Brand name | INCI name | Preferred Supplier | % |
| PHASE-A (OIL) | | | |
| Cetiol CC | Dicaprylyl carbomate | BASF Care Creations | 0.5 |
| Cetiol OE | Dicaprylyl ether | " | 1.5 |
| Olivem 1000 | Cetearyl olivate sorbitan olivate | Hall Star Italica | 1.5 |
| Olivem Vs Feel | Cetearyl alcohol, cetyl palmitate, sorbitan palmitate, sorbitan oleate | Hall Star Italica Clariant Personal Care | 1.5 1.5 |
| Vegetal squalane | Squalane | Evonik Personal care | |
| Ceramides III | Ceramides | Organic Creations Inc | 0.05 |
| Kokum butter | *Garcinia indica* butter | Dr Adorable | 0.4 |
| Black currant oil | *Ribes nigrum* oil | Dr Adorable | 0.5 |
| Chia seed oil | *Salvia hispanica* seed oil | Mountain rose herbs | 0.5 |
| Borage seed oil | *Borago officianalis* seed oil | Mountain rose herbs | 0.5 |
| Evening primrose oil | *Oenothera biennis* oil | Extract & Ingredients Ltd | 0.5 |
| Pomegranate oil | *Punica granatum* oil | | 0.5 |
| Fractionated coconut oil | *Cocus nucifera* oil | Dr Adorable | 1.0 |
| Lanette 22 | Behenyl alcohol | BASF Care Creations | 0.35 |
| Vitamin E | Tocopheryl acetate | DSM specialty products | 0.05 |
| Lexfeel N5 | Diheptyl succinate (and) caproyloyl glycerin/sebacic acid copolymer | Inolex Personal Care | 1.5 |
| Tegosoft P | Isopropyl Palmitate | Evonik Personal care | 1.5 |
| Tegocare 450 | Polyglyceryl-3 Methylglucose Distearate | Evonik Personal care | 2.0 |

TABLE 2-continued

Face lotion formulation comprising Lf Qi6 bioextracts

| Trade/Brand name | INCI name | Preferred Supplier | % |
|---|---|---|---|
| PHASE-B (WATER) | | | |
| Distilled Water | Aqua | — | 79.2 |
| Soft xanthan gum | Soft xanthan gum | CP Kelco or lotion-crafter | 0.28 |
| Glycerin (vegetable) | Glycerin | Natures Answer | 3.0 |
| *Aloe vera* 1x | *Aloe Barbadensis* ext | Making Cosmetics Inc | 1.0 |
| Xylitol | Xylitol | " | 0.1 |
| Vitamin b3 | Niacinamide | " | 0.5 |
| Vitamin b5 | Panthenol | DSM | 0.5 |
| Citric acid | — | DSM | 0.01 |
| PRESERVATIVES | | | |
| Geogard Ultra | Gluconolactone and Sodium Benzoate | Lonza | 0.4 |
| Geogard 221 | Dehydroxyacetic & Benzoic acid | Lonza | 0.4 |
| ACTIVES | | | |
| Qi6 (*Lactobacillus* ferment) | Proprietary active | Quorum Innovations | 0.025 |
| NMF | Proprietary active | Quorum Innovations | 0.2 |
| FRAGRANCE MIX | | | |
| Frangipani oil | *Plumeria alba* essential oil | Eden Gardens | 0.5 |
| Jasmine oil | *Jasminum grandiflorum* essential oil | " | |
| Sandal wood oil | *Santalum album* essential oil | " | |

The formulation of the natural moisturizing factor (NMF) is provided in Table 4. The face lotion was prepared using the following procedures. The oil phase (except the cermaides) was warmed to 75° C. with constant stirring. The aqueous phase was warmed to 70° C. At an optimal temperature, e.g. 70° C., the oil phase was slowly added to the aqueous phase and the mixture was allowed to emulsify, with constant stirring, at 70-75° C. for 10 minutes. The mixture was subsequently cooled, while stirring, to around 45-50° C. The ceramides, preservatives, actives, and fragrance mix were added to the mixture and stirred for another 10 minutes. The mixture was then further mixed with a hand-held blender for approximately 2-4 minutes, followed by vigorous mixing in a vacuum mixer for 4 minutes. The resulting lotion blend was cooled to room temperature and packaged into bottles. The typical properties of the face lotion are presented in the following table.

TABLE 3

Typical properties of the face lotion.

| Appearance | White liquid emulsion, readily flows |
|---|---|
| Brookfiled viscosity at 25° C. | Medium viscosity at 20,000 cps (LV-3 spindle) |
| pH at 25° C. | 4.5-5.0 |
| Storage stability | 1 month (4° C., 25° C. at 45° C.) |
| Prospective fragrance | Natural earthy |

TABLE 4

The formulation of NMFx ™.

| Chemical | gms/85.9 gms |
|---|---|
| Free Amino Acids | |
| Serine | 18.2 |
| Arginine | 9.1 |
| Glutamic acid | 3.2 |
| Tyrosine | 2.3 |
| Alanine | 6.6 |
| Sugars | |
| Xylitol | 4.5 |
| Sucrose | 4.0 |
| Bases | |
| Creatine monohydrate | 1.0 |
| Glucosamine | 0.5 |
| Acids | |
| Pyrrolidone carboxylic acid | 12 |
| Hyaluronic acid | 1.0 |
| Minerals | |
| Sodium chloride | 5.0 |
| Sodium lactate | 5.0 |
| Potassium citrate | 0.5 |
| Calcium chloride | 1.5 |
| Magnesium chloride | 1.5 |
| Actives | |
| L-theonine | 5 |
| Ceramides | 5 |

TABLE 5

The formulation of an eye cream comprising Lf Qi6 bioextracts.

| Trade/Brand name | INCI name | Preferred Supplier | (%) |
|---|---|---|---|
| PHASE-A (OIL) | | | |
| Cetiol CC | Dicaprylyl carbomate | BASF Care Creations | 0.5 |
| Cetiol OE | Dicaprylyl ether | " | 1.5 |
| Olivem 1000 | Cetearyl olivate sorbitan olivate | Hall Star Italica | 1.65 |
| Olivem Vs Feel | Cetearyl alcohol, cetyl palmitate, sorbitan palmitate, sorbitan oleate | Hall Star Italica | 1.65 |
| Olive squalane | Squalane | Clariant Personal Care | 1.5 |
| Ceramides III | Ceramides | Evonik Personal care | 0.05 |
| Kokum butter | *Garcinia indica* butter | Organic Creations Inc | 0.65 |
| Black currant oil | *Ribes nigrum* oil | Dr Adorable | 0.5 |
| Chia seed oil | *Salvia hispanica* seed oil | Dr Adorable | 0.5 |
| Borage seed oil | *Borago officianalis* seed oil | Mountain rose herbs | 0.5 |
| Evening primrose oil | *Oenothera biennis* oil | Mountain rose herbs | 0.5 |
| Pomegranate oil | *Punica granatum* oil | Extract & Ingredients Ltd | 0.5 |
| Fractionated coconut oil | *Cocus nucifera* oil | | 1.0 |
| Lanette 22 | Behenyl alcohol | Dr Adorable | 0.35 |
| Vitamin E | Tocopheryl acetate | BASF Care Creations | 0.05 |
| Lexfeel N5 | Diheptyl succinate (and) capryloyl glycerin/sebacic acid copolymer | DSM specialty products Inolex Personal Care | 1.7 |
| Tegosoft P | Isopropyl Palmitate | | 1.6 |
| Tegocare 450 | Polyglyceryl-3 Methylglucose Distearate | Evonik Personal care Evonik Personal care | 2.0 |
| PHASE-B (WATER) | | | |
| Distilled Water | Aqua | | 78.2 |
| Soft xanthan gum | Soft xanthan gum | — | 0.29 |
| Glycerin (vegetable) | Glycerin | CP Kelco or lotioncrafter | 3.0 |
| *Aloe vera* 1x | *Aloe Barbadensis* ext | | 1.0 |
| Xylitol | Xylitol | Natures Answer | 0.1 |
| Vitamin b3 | Niacinamide | Making Cosmetics Inc | 0.5 |
| Vitamin b5 | Panthenol | " | 0.5 |
| Citric acid (pH) | — | DSM | 0.01 |
| PRESERVATIVES | | | |
| Geogard Ultra | Gluconolactone and Sodium Benzoate | DSMLonza | 0.4 |
| Geogard 221 | Dehydroxyacetic & Benzoic acid | Lonza | 0.4 |
| ACTIVES | | | |
| Qi6 (*Lactobacillus* ferment) | Proprietary active | Quorum Innovations | 0.05 |
| NMF | Proprietary active | Quorum Innovations | 0.20 |
| FRAGRANCE MIX | | | |
| Lavender oil | *Lavandula angustifolio* essential oil | Eden Gardens | 0.4 |

The eye cream was prepared using the following procedures. The oil phase (except the cermaides) was warmed to 75° C. with constant stirring. The aqueous phase was warmed to 70° C. At an optimal temperature, e.g. 70° C., the oil phase was slowly added to the aqueous phase and the mixture was allowed to emulsify, with constant stirring, at 70-75° C. for 10 minutes. The mixture was subsequently cooled, while stirring, to around 45-50° C. The ceramides, preservatives, actives, and fragrance mix were added to the mixture and stirred for another 10 minutes. The mixture was then further mixed with a hand-held blender for approximately 2-4 minutes, followed by vigorous mixing in a vacuum mixer for 4 minutes. The resulting lotion blend was cooled to room temperature and packaged into bottles. The typical properties of the eye cream are presented in the following table.

TABLE 6

Typical properties of the eye cream.

| | |
|---|---|
| Appearance | White liquid emulsion, readily flows |
| Brookfiled viscosity at 25° C. | Medium viscosity at 30,000 cps (LV-3 spindle) |
| pH at 25° C. | 4.5-5.0 |
| Storage stability | 1 month (4° C., 25° C. at 45° C.) |
| Prospective fragrance | Natural earthy |

TABLE 7

The formulation of a serum comprising the Lf Qi6 bioextracts.

| Ingredients | % |
|---|---|
| Water | 81.6 |
| *Aloe vera* (10x) | 2.0 |
| Citric acid | 0.01 |
| Glycerin (Vegetable) | 2.0 |
| Xylitol | 0.5 |
| Green Tea Extract | 0.5 |
| Golden seal extract | 0.5 |
| Hyaluronic acid BT (DSM) | 0.5 |

TABLE 7-continued

The formulation of a serum comprising the Lf Qi6 bioextracts.

| | % |
|---|---|
| Thickner (Structure cell 12000) cellulose based | 0.15 |
| Phytoterra mate (Lonza) | 0.1 |
| Panthenol (DSM) | 1.0 |
| Niacinamide (DSM) | 1.0 |
| Allantoin (Ashland) | 0.05 |
| L-Theanine (Bulk Naturals) | 0.1 |
| Geogard Ultra (Lonza) | 0.4 |
| Geogard 221 (Lonza) | 0.4 |
| Vitamin E | 0.1 |
| FRAGRANCES | |
| Jasmine oil (*Jasminium grandiflorum*) | 0.6 |
| Frankincense (*Boswellia carterii*) | |
| Lavender (*Lavandula angustifolio*) | |
| ACTIVES | |
| Qi6 (*Lactobacillus* ferment) | 0.025 |
| NMF (moisturizing complex, minerals) | 0.05 |

The serum was prepared by mixing the ingredients listed in Table 7, in the order presented therein, with gentle stirring to allow the hyaluronic acid to fully hydrate and be incorporated in the mixture. The pH was adjusted to approximately 4.5-5.0 using citric acid. The typical properties of the serum are listed in Table 8.

TABLE 8

Typical properties of the serum.

| Appearance | Light brown liquid |
|---|---|
| Brookfiled viscosity at 25° C. | Low viscosity at 1500-2000 cps (LV-3 spindle) |
| pH at 25° C. | 4.5-5.0 |
| Storage stability | 1 month (4° C., 25° C. at 45° C.) |
| Prospective fragrance | Natural earthy |

TABLE 9

The formulation of a face-wash comprising the Lf Qi6 bioextract.

| Trade Name | INCI Name (or generic name) | % |
|---|---|---|
| Aqua | — | 30.0 |
| Miranol Ultra L 32 (solvay) | Sodium lauroampho acetate (Solvay) | 25.0 |
| MiraCare Plaisant (solvay) | Sodium cocoyl Isethionate + Sodium lauramphoacetate | 25.0 |
| Planteron 2000 (BASF) | Decyl glucosides | 10.0 |
| Glycerin | Vegetable (Jedwards) | 2.5 |
| Amaranth S | Sodium cocyl hydrolyzed Amaranth ext (Lonza) | 2.0 |
| Xylitol | Xylitol (Spectrum chemicals) | 0.5 |
| Panthenol (DSM) | — | 0.5 |
| Niacinamide (DSM) | — | 0.5 |
| *Aloe vera* | *Aloe vera* | 3.0 |
| Geogard Ultra | Gluconolactone + Sodium Benzoate | 0.45 |
| Geogard 221 | Dehydroxyacetic & Benzoic acid | 0.45 |
| Citric acid (pH Adjuster) | — | 0.76 |
| Qi6 (*Lactobacillus* ferment) | *Lactobacillus* ferment | 0.001 |
| NMF | Qi-NMF Moisturizing complex | 0.075 |
| Fragrance mix (Lavender oil:Spearmint 6:1) | *Lavandula angustifolio, Mentha spicata* | 0.45 |

The face-wash was prepared using the following procedures. Water was first added into a mixing vessel and the vessel was turned on to low speed (100-150 rpm). Xylitol, panthenol, niacinamide, NMF, Geogard Ultra was sequentially added and dissolved in water. Geogard 221 and Lf Qi6 bioextracts were subsequently added to the mixture. MiraCare Plaisant was then added to the mixture and stirred until the mixture turned clear. Miranol Ultra 32 was added to the mixture and stirred until the mixture turned clear, which was followed by the addition of Plaanteron 2000 to the mixture. The mixture was then stirred until it turned clear and its pH was subsequently adjusted using citric acid. The typical properties of the face-wash are listed in Table 10 below.

TABLE 10

Typical properties of the face-wash.

| Appearance | Clear viscous liquid |
|---|---|
| Brookfiled viscosity at 25° C. | 6000-8000 cps (LV-3 spindle, 12 rpm) |
| pH at 25° C. | 6.5-7.0 |
| Storage stability | 1 month (4° C., 25° C. at 45° C.) |
| Prospective fragrance | Natural minty |

EXAMPLE 9

Treatment of Eosinophilic Gastrointestinal Diseases

Eosinophilic gastrointestinal diseases have risen in incidence significantly in the past few decades. Of these diseases, eosinophilic esophagitis is the most common. Current treatments are difficult and/or involve systemic steroid exposure. For instance, an elemental diet free of food allergen such as milk, wheat, seafood and soy is effective but burdensome to the patient. Therefore, oral slurries of topical steroids are often used. This has the advantage of delivering the therapeutic component directly to the inflamed tissues. Despite its efficacy, oral steroids can have potential side effects, such as immunosuppression, growth velocity reduction, and adverse bone density effects. There is an immediate need for effective, non-burdensome, steroid-free treatments for eosinophilic gastrointestinal disease. Mucoadhesives are advantageously used to increase local tissue exposure to the active components of the formulation. Here we describe a pharmaceutical formulation of a stable, high-viscosity orally-administered gel containing a *Lactobacillus* extract. A steroid such as budesonide (e.g., 0.01% of total formulation) may be added if desired.

| | |
|---|---|
| *Lactobacillus* extract | 0.001-0.5 g |
| Parabens | 0.5 g |
| Propylene glycol | 5 g |
| *Lutrol F127 | 20 g |
| Water | 75 g |
| Total: | 100 g |

Dissolve Lutrol F127 and parabens in water heated to 80 degrees C.
Add propylene glycol and *lactobacillus* extract.
Keep heated until a clear colorless gel is obtained.

*Alternative mucoadhesives may be used, such as carboxymethyl cellulose, hydroxypropyl methyl cellulose, or hydrodroxypropyl cellulose.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

1. Irvine A D, McLean W H, Leung D Y. Filaggrin mutations associated with skin and allergic diseases. N Engl J Med 2011: 365: 1315-1327.
2. Leung D Y, Bieber T. Atopic dermatitis. Lancet 2003: 361: 151-160
3. Malajian D, Guttman-Yassky E. New pathogenic and therapeutic paradigms in atopic dermatitis. Cytokine 2014 Dec. 23: pii: S1043-4666(14)00606-1.
4. Leung D Y, Guttman-Yassky E. Deciphering the complexities of atopic dermatitis: shifting paradigms in treatment approaches. J Allergy Clin Immunol 2014: 134 (4): 769-779.
5. Peng W, Novak N. Pathogenesis of atopic dermatitis. Clin Exp Allerg 2015: 45 (3): 566-574.
6. Boguniewicz M, Leung D Y M. Atopic Dermatitis: a disease of altered skin barrier and immune dysregulation. Immunol Rev 2011 July: 242(1): 233-246.
7. Seguchi T, Chang-Yi C, Kusuda S et al. Decreased expression of filaggrin in atopic dermatitis. Arch Dermatol Res 1996: 288: 442-446.
8. Thyssen J P. Atopic dermatitis, filaggrin mutations and irritant contact dermatitis. Br J Dermatol 2013: 168: 233-234.
9. Howell M D, Kim B E, Gao P et al. Cytokine modulation of atopic dermatitis filaggrin skin expression. J Allergy Clin Immunol 2007: 120: 150-155.
10. Niebuhr M, Heratizadeh A, Wickmann K et al. Intrinsic alterations of pro-inflammatory mediators in unstimulated and TLR-2 stimulated keratinocytes from atopic dermatitis patients. Exp Dermatol 2011: 20: 468-472.
11. Leung D Y, Harbeck R, Bina P et al. Presence of IgE antibodies to staphylococcal exotoxins on the skin of patients with atopic dermatitis. J Clin Invest 1993: 92: 1374-1380.
12. Boguniewicz M. New strategies for dealing with *Staphylococcus aureus* colonization and the emerging methicillin-resistant *Staphylococcus aureus* epidemic in atopic dermatitis. Chem Immunol Allergy 2012: 96: 113-119.
13. Suh L, Coffin S, Leckerman K H et al. Methicillin-resistant *Staphylococcus aureus* colonization in children with atopic dermatitis. Pediatr Dermatol 2008: 25(5): 528-534.
14. Findley K, Grice E A. The Skin microbiome: a focus on pathogens and their association with skin disease. PLoS Pathog 2014: 10(11): e1004436. doi:10.1371/journal.ppat.1004436.
15. Higaki S, Morohashi M, Yamagishi T et al. Comparative study of staphylococci from the skin of atopic dermatitis patients and from healthy subjects. Int J Dermatol 1999: 38: 265-269.
16. van Drongelen V, Haisma E M, Out-Luiting J J et al. Reduced filaggrin expression is accompanied by increased *Staphylococcus aureus* colonization of epidermal skin models. Clin Exp Allergy 2014: 44(12): 1515-1524.
17. Ong P Y, Ohtake T, Brandt C et al. Endogenous antimicrobial peptides and skin infections in atopic dermatitis. N Eng J Med 2002: 347: 1151-1160.
18. Zeeuwen P L, Boekhorst J, van den Bogaard E H et al. Microbiome dynamics of human epidermis following skin barrier disruption. Genome Biol 2012: 13(11): R101.
19. Oh J, Byrd A L, Deming C et al. Biogeography and individuality shape function in the human skin metagenome. Nature 2014: 514(7520): 59-64.
20. Belkaid Y, Segre J A. Dialogue between skin microbiota and immunity. Science 2014: 346(6212): 954.
21. Baviera G, Leoni M C, Capra L et al. Microbiota in healthy skin and in atopic eczema. Biomed Res Int 2014: 436921.
22. Kong H H, Oh J, Deming C et al. Temporal shifts in the skin microbiome associated with disease flares and treatment in children with atopic dermatitis. Genome Res 2012: 22: 850-859.
23. Felten A, Grandry B, Lagrange P H et al. Evaluation of Three Techniques for Detection of Low-Level Methicillin-Resistant *Staphylococcus aureus* (MRSA): a Disk Diffusion Method with Cefoxitin and Moxalactam, the Vitek 2 System, and the MRSA-Screen Latex Agglutination Test. J Clin Microbiol 2002: 40 (8): 2766-2771.
24. Subhadra B, Krier J, Hofstee K et al. Draft whole-genome sequence of *Lactobacillus fermentum* LfQi6, derived from the human microbiome. Genome Announc 2015: 3(3): e00423-15. doi:10.1128/genomeA.00423-15.
25. Conlan S, Mijares L A, NISC Comparative Sequencing Program et al. *Staphylococcus epidermidis* pan-genome sequence analysis reveals diversity of skin commensal and hospital infection-associated isolates. Genome Biol 2012: 13(7): R6
26. Sugimoto S, Iwase T, F. Sato F et al. Cloning, expression and purification of extracellular serine protease Esp, a biofilm-degrading enzyme, from *Staphylococcus epidermidis*. J Appl Microbiol 2011: 111: 1406-1415.
27. Hochstim C J, Choi J Y, Lowe D et al. Biofilm detection with hematoxylin-eosin staining. Arch Otolaryngol Head Neck Surg. 2010: 136(5): 453-456
28. Tuominen V J, Ruotoistenmaki S, Viitanen A et al. ImmunoRatio: a publicly available web application for quantitative image analysis of estrogen receptor (ER), progesterone receptor (PR), and Ki-67. Breast Cancer Res 2010: 12(4): R56.
29. Williams R E, Gibson A G, Aitchison T C et al. Assessment of a contact-plate sampling technique and subsequent quantitative bacterial studies in atopic dermatitis. Br J Dermatol 1990: 123(4): 493-501.
30. Goh C-L, Goh, Wong J S et al. Skin colonization of *Staphylococcus aureus* in atopic dermatitis patients seen at the National Skin Centre, Singapore. Int J Dermatol 1997: 36(9): 653-657.
31. Travers J B, Kozman A, Mousdicas N et al. Infected Atopic Dermatitis Lesions Contain Pharmacologic Amounts of Lipoteichoic Acid. J Allergy Clin Immunol 2010 January: 125(1): 146.

32. Michelsen K S, Aicher A, Mohaupt M et al. The role of toll-like receptors (TLRs) in bacteria-induced maturation of murine dendritic cells (DCS). Peptidoglycan and lipoteichoic acid are inducers of DC maturation and require TLR2. J Biol Chem 2001: 276: 25680-25686

33. Lemjabbar H, Basbaum C. Platelet-activating factor receptor and ADAM10 mediate responses to *Staphylococcus aureus* in epithelial cells. Nature Med 2002: 8: 41-46.

34. Zhang Q, Mousdicas N, Yi Q et al. Staphylococcal lipoteichoic acid inhibits delayed-type hypersensitivity reactions via the platelet-activating factor receptor. J Clin Invest 2005: 115: 2855-2861.

35. Hattar K, Grandel U, Moeller A et al. Lipoteichoic acid (LTA) from *Staphylococcus aureus* stimulates human neutrophil cytokine release by a CD14-dependent, Toll-like-receptor-independent mechanism: Autocrine role of tumor necrosis factor-[alpha] in mediating LTA-induced interleukin-8 generation. Crit Care Med 2006: 34(3): 835-841.

36. Heinemann C, van Hylckama Vlieg J E, Janssen D B et al. Purification and characterization of a surface-binding protein from *Lactobacillus fermentum* RC-14 that inhibits adhesion of *Enterococcus faecalis* 1131. FEMS Microbiol Lett 2000: 190(1): 177-180.

37. de la Fuente-Núñez C, Reffuveille F, Haney E F et al. Broad-spectrum anti-biofilm peptide that targets a cellular stress response. PLoS Pathog 2014: 10(5): e1004152.

38. Haney E F, Mansour S C, Hilchie A L et al. High throughput screening methods for assessing antibiofilm and immunomodulatory activities of synthetic peptides. Peptides 2015: S0196-9781(15): 00073-X.

39. Kim M S, Kim J E, Yoon Y S et al. Improvement of atopic dermatitis-like skin lesions by IL-4 inhibition of P14 protein isolated from *Lactobacillus casei* in NC/Nga mice. Appl Microbiol Biotechnol 2015 [Epub ahead of print]

40. Iwase T, Uehara Y, Shinji H et al. *Staphylococcus epidermidis* Esp inhibits *Staphylococcus aureus* biofilm formation and nasal colonization. Nature 2010: 465 (7296): 346-349. doi: 10.1038/nature09074.

41. Sugimoto S, Iwamoto T, Takada K et al. *Staphylococcus epidermidis* Esp degrades specific proteins associated with *Staphylococcus aureus* biofilm formation and host-pathogen interaction. J Bacteriol 2013: 195(8): 1645-1655.

42. Li D, Lei H, Li Z et al. A novel lipopeptide from skin commensal activates TLR2/CD36-p38 MAPK signaling to increase antibacterial defense against bacterial infection. PLoS One 2013: 8(3): e58288.

43. Lai Y, Cogen A L, Radek K A et al. Activation of TLR2 by a small molecule produced by *Staphylococcus epidermidis* increases antimicrobial defense against bacterial skin infections. J Invest Dermatol 2010: 130(9): 2211-2221.

44. Wang Y, Kuo S, Shu M et al. *Staphylococcus epidermidis* in the human skin microbiome mediates fermentation to inhibit the growth of *Propionibacterium acnes*: implications of probiotics in acne vulgaris. Appl Microbiol Biotechnol 2014: 98(1): 411-424. doi: 10.1007/s00253 013-5394-8. nature09074.

45. Naik S, Bouladoux N, Wilhelm C et al. Compartmentalized control of skin immunity by resident commensals. Science 2012: 337(6098): 1115-1119. doi: 10.1126/science.1225152.

46. Krishnan A, Nair S A, Pillai M R, Biology of PPAR gamma in cancer: a critical review on existing lacunae. Curr Mol Med 2007: 7(6): 532-40. doi:10.2174/156652407781695765. PMID 17896990.

What is claimed is:

1. A method for inhibiting microbial growth on a surface or in a composition, wherein the method comprises applying to the surface or composition a microbial growth-inhibiting amount of a preparation comprising a bioactive *Lactobacillus fermentum* strain having an Accession No. PTA-122195 grown as a biofilm.

2. The method, according to claim 1, wherein the surface is skin.

3. The method, according to claim 2, wherein skin barrier function is enhanced.

4. The method, according to claim 2, wherein the preparation acts as an agonist of PPAR.

5. The method, according to claim 1, wherein the preparation further comprises alcohol.

6. The method, according to claim 1, wherein the method promotes the growth of commensal bacteria.

7. The method according to claim 6, wherein the commensal bacteria are *Staphylococcus epidermidis*.

8. The method, according to claim 1, wherein the surface is an inanimate surface.

9. The method, according to claim 1, wherein the method inhibits the growth of methicillin-resistant *Staphylococcus aureus* (MRSA).

10. The method, according to claim 1, wherein the preparation is edible.

* * * * *